(12) United States Patent
Liang et al.

(10) Patent No.: US 12,029,781 B2
(45) Date of Patent: Jul. 9, 2024

(54) GENE FOR TRYPSIN-LIKE SERINE PROTEASE, A PROTEIN ENCODED THEREBY AND USE THEREOF

(71) Applicant: GUANGDONG OCEAN UNIVERSITY, Zhanjiang (CN)

(72) Inventors: Haiying Liang, Zhanjiang (CN); Junjun He, Zhanjiang (CN); Chenghao Shen, Zhanjiang (CN); Xiaochen Fang, Zhanjiang (CN); Jinzhao Lu, Zhanjiang (CN)

(73) Assignee: GUANGDONG OCEAN UNIVERSITY, Zhanjiang (CN)

( * ) Notice: Subject to any disclaimer, the term of this patent is extended or adjusted under 35 U.S.C. 154(b) by 502 days.

(21) Appl. No.: 17/430,328

(22) PCT Filed: Nov. 27, 2020

(86) PCT No.: PCT/CN2020/132289
§ 371 (c)(1),
(2) Date: Aug. 12, 2021

(87) PCT Pub. No.: WO2021/258637
PCT Pub. Date: Dec. 30, 2021

(65) Prior Publication Data
US 2022/0313797 A1    Oct. 6, 2022

(30) Foreign Application Priority Data
Jun. 24, 2020 (CN) .......................... 202010589361.X

(51) Int. Cl.
*A61P 31/04* (2006.01)
*A61K 38/48* (2006.01)
*C12N 9/76* (2006.01)

(52) U.S. Cl.
CPC ............ *A61K 38/482* (2013.01); *A61P 31/04* (2018.01); *C12Y 304/21004* (2013.01)

(58) Field of Classification Search
CPC .................. A61K 38/482; A61P 31/04; C12Y 304/21004; C12Y 304/21106; C12N 9/6427
See application file for complete search history.

(56) References Cited

PUBLICATIONS

Linag H., "Cloning and functional analysis of a trypsin-like serine protease from Pinctada fucata martensii", Fish and Shellfish Immunology, vol. 126 (2022), pp. 327-335. (Year: 2022).*
Shen C., "Gene cloning and functional study of PmKSPI from Pinctada fucata martensii", Fish and Shellfish Immunology, vol. 131 (2022), pp. 1157-1165. (Year: 2022).*

* cited by examiner

*Primary Examiner* — Satyendra K Singh
(74) *Attorney, Agent, or Firm* — Adam Warwick Bell

(57) ABSTRACT

Provided is a gene for trypsin-like serine protease, a protein encoded thereby and use thereof. The nucleotide sequence of the gene for trypsin-like serine protease is set forth in SEQ ID No. 1, the amino acid sequence of the protein encoded by the gene for trypsin-like serine protease is set forth in SEQ ID No. 2. The protein encoded by the gene provided by the present disclosure is capable of inhibiting *P. aeruginosa*, *A. hydrophila*, *V. parahaemolyticus* and *V. harveyi*.

2 Claims, 17 Drawing Sheets

Specification includes a Sequence Listing.

```
Pinctada_fuscata_martensii   .........................................................    0
Crassostrea_gigas            KGGVRKIRVIIHPKFAERSSYDNEIALIEMDEAVNFF.                         112
Eurythma_scolopes            VGGLQVQMKSIILRPSENKSSVEDSDIAIVEFYERLHFS.                        108
Octopus_vulgaris             HGGIRVQMKHWIVRPAFN.EITEDSDIBVIVLKEIDFT.                         106
Mizuhopecten_yessoensis      DQYMQTYRADHILVRPEFELDLLDNEIALVRIDTPISFF.                        116
Sinonovacula_constricta      VITGNIVRVIGIYPRHYSDTSKHEIALMRLSKRINIDI                          105
Azumapecten_farreri          IYISQIHSAVNIISHQGYDRRTHRNIAIIVRLEKPIDIFS                        103
Hyriopsis_cumingii           DFNQRLYLIRKVIIHPGYNVISLKDIIALIIIQEPIEYN.                        115
Consensus                    
```

FIG. 3C

|  |  |  |
|---|---|---|
| Pinctada_fucata_martensii | .......................................... | 0 |
| Crassostrea_gigas | DKIQPICKPTSIIDDI.FLSRRGGRRVGRVIGCGQRYEN | 151 |
| Euprymna_scolopes | RNIRRICIVDKAVIEEVAEYSGVYG....TDVYGCGITSNG | 144 |
| Octopus_vulgaris | PYVHPICIVNNEVIGES.EYSGFYG....TDVYGCGETAFG | 141 |
| Mizuhopecten_yessoensis | DHAQFYCIFGQDAKGEDKCIITGWGRQKKFYFASGGIFKL | 156 |
| Sinonovacula_constricta | TYTRDACIFSAYETFDS......DVCIYSGWGMTHYD | 136 |
| Azumapecten_farreri | INVRIACIFEPHQIEDN......VWCIATGWGTTYLG | 134 |
| Hyriopsis_cumingii | DHTRPACIFDASHHYRVG......DVCIFGWGSTITT | 147 |
| Consensus |  |  |

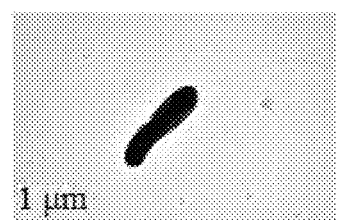
FIG. 17A
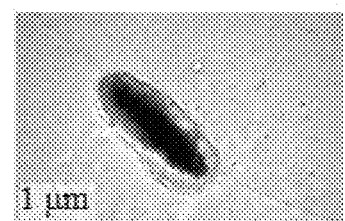
FIG. 17B
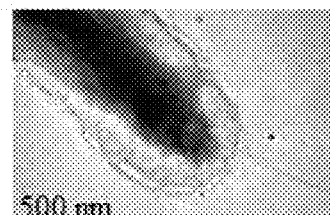
FIG. 17C
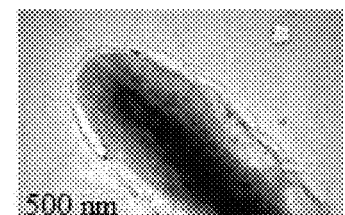
FIG. 17D
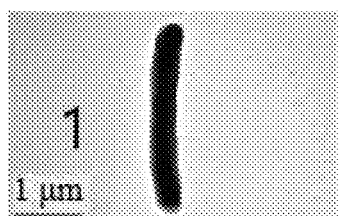
FIG. 17E
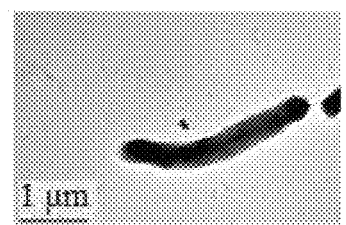
FIG. 17F
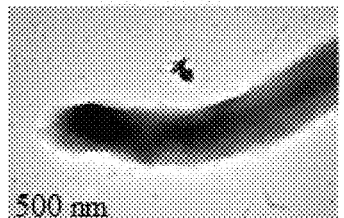
FIG. 17G
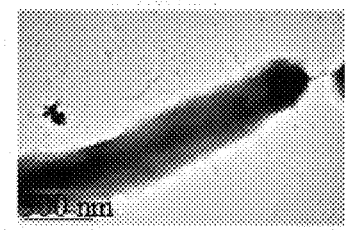
FIG. 17H
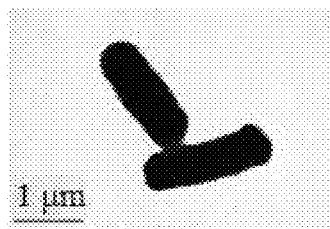
FIG. 17I
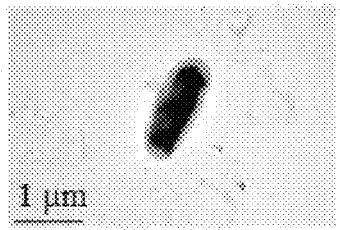
FIG. 17J
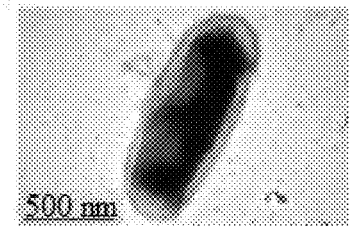
FIG. 17K
FIG. 17

SEQUENCE LISTING

```
<160> NUMBER OF SEQ ID NOS: 22

<210> SEQ ID NO 1
<211> LENGTH: 778
<212> TYPE: DNA
<213> ORGANISM: Artificial Sequence
<220> FEATURE:
<223> OTHER INFORMATION: gene for trypsin-like serine protease

<400> SEQUENCE: 1
acatgggcta ataaatggat cgtgacagcc gcccactgta tcgtgcgttt tcccgagaaa      60
ttccacgaat tgttccaccc ctctaaggtc acccttatta ttggtacaga gcagtgtagc     120
ggatatgacg gccaaatcgt ggacatcgag tcatatgttg tgcatcctag atttgcagaa     180
agggctccat acgaccatga tatagctttg atagaacttc gtcaagattt aaactttaca     240
gaacgtgtac aaccaatatg tctcaagcag ccggattacg tgaatactgc tttccttcat     300
cgcaaagtcg ggcgtaaggc agggaggggtt gtagggtgtg gtcaattgta tgaaaatgta    360
gatgctatac ccacggagct acatgacgtt ttcgtaccaa cagtgactag ggagaaatgt     420
atggaggcgg acatagggcg aggaaatttc actgacacta tgttctgcgc agggtatgac     480
agggctttat tcggagatgc ttgttatggt gatagtggtg gctctttggc gatgaatgac     540
tccccatttg accoctgggt ccttgtgggc gtggtgtcat ggggagttgg gtgtgaccga     600
caaggacatt atggatacta tacaaatata gctcactttt ataactggat acaaaatgtc     660
acaaatgttt taaataatta ggattgaaac aataaagaga tatagatctt aatttatact     720
attgagacac aattaaaaaa agtttaaccc taaaaaaaaa aaaaaaaaaa aaaaaaa        778

<210> SEQ ID NO 2
<211> LENGTH: 86
<212> TYPE: PRT
<213> ORGANISM: Artificial Sequence
<220> FEATURE:
<223> OTHER INFORMATION: amino acid sequence of the protein
```

```
<400> SEQUENCE: 2

Met Glu Ala Asp Ile Gly Arg Gly Asn Phe Thr Asp Thr Met Phe Cys
1               5                   10                  15

Ala Gly Tyr Asp Arg Ala Leu Phe Gly Asp Ala Cys Tyr Gly Asp Ser
            20                  25                  30

Gly Gly Ser Leu Ala Met Asn Asp Ser Pro Phe Asp Pro Trp Val Leu
        35                  40                  45

Val Gly Val Val Ser Trp Gly Val Gly Cys Asp Arg Gln Gly His Tyr
    50                  55                  60

Gly Tyr Tyr Thr Asn Ile Ala His Phe Tyr Asn Trp Ile Gln Asn Val
65              70                  75                  80

Thr Asn Val Leu Asn Asn
                85

<210> SEQ ID NO 3
<211> LENGTH: 21
<212> TYPE: DNA
<213> ORGANISM: Artificial Sequence
<220> FEATURE:
<223> OTHER INFORMATION: Primer PmTLS-3'-inner

<400> SEQUENCE: 3
tatggaggcg gacatagggc g                                       21

<210> SEQ ID NO 4
<211> LENGTH: 21
<212> TYPE: DNA
<213> ORGANISM: Artificial Sequence
<220> FEATURE:
<223> OTHER INFORMATION: Primer PmTLS-3'-outer

<400> SEQUENCE: 4
catcgcaaag tcgggcgtaa g                                       21

<210> SEQ ID NO 5
<211> LENGTH: 23
<212> TYPE: DNA
<213> ORGANISM: Artificial Sequence
<220> FEATURE:
<223> OTHER INFORMATION: Primer PmTLS-5'-inner

<400> SEQUENCE: 5
tgtccgcctc catacatttc tcc                                     23

<210> SEQ ID NO 6
<211> LENGTH: 20
<212> TYPE: DNA
<213> ORGANISM: Artificial Sequence
<220> FEATURE:
<223> OTHER INFORMATION: Primer PmTLS-5'-outer

<400> SEQUENCE: 6
atgacaccac gcccacaagg                                         20

<210> SEQ ID NO 7
<211> LENGTH: 24
<212> TYPE: DNA
<213> ORGANISM: Artificial Sequence
<220> FEATURE:
<223> OTHER INFORMATION: M13-F

<400> SEQUENCE: 7
cgccagggtt ttcccagtca cgac                                    24
```

<210> SEQ ID NO 8
<211> LENGTH: 24
<212> TYPE: DNA
<213> ORGANISM: Artificial Sequence
<220> FEATURE:
<223> OTHER INFORMATION: Primer M13-R

<400> SEQUENCE: 8
gagcggataa caatttcaca cagg                                           24

<210> SEQ ID NO 9
<211> LENGTH: 20
<212> TYPE: DNA
<213> ORGANISM: Artificial Sequence
<220> FEATURE:
<223> OTHER INFORMATION: Primer PmTLS-RT-F

<400> SEQUENCE: 9
agaaatgtat ggaggcggac                                                20

<210> SEQ ID NO 10
<211> LENGTH: 22
<212> TYPE: DNA
<213> ORGANISM: Artificial Sequence
<220> FEATURE:
<223> OTHER INFORMATION: Primer PmTLS-RT-R

<400> SEQUENCE: 10
accataacaa gcatctccga at                                             22

<210> SEQ ID NO 11
<211> LENGTH: 20
<212> TYPE: DNA
<213> ORGANISM: Artificial Sequence
<220> FEATURE:
<223> OTHER INFORMATION: Primer GAPDH-F

<400> SEQUENCE: 11
gcagatggtg ccgagtatgt                                                20

<210> SEQ ID NO 12
<211> LENGTH: 21
<212> TYPE: DNA
<213> ORGANISM: Artificial Sequence
<220> FEATURE:
<223> OTHER INFORMATION: Primer GAPDH-R

<400> SEQUENCE: 12
cgttgattat cttggcgagt g                                              21

<210> SEQ ID NO 13
<211> LENGTH: 86
<212> TYPE: PRT
<213> ORGANISM: Pinctada fucata

<400> SEQUENCE: 13

Met Glu Ala Asp Ile Gly Arg Gly Asn Phe Thr Asp Thr Met Phe Cys
1               5                   10                  15

Ala Gly Tyr Asp Arg Ala Leu Phe Gly Asp Ala Cys Tyr Gly Asp Ser
            20                  25                  30

Gly Gly Ser Leu Ala Met Asn Asp Ser Pro Phe Asp Pro Trp Val Leu
        35                  40                  45

Val Gly Val Val Ser Trp Gly Val Gly Cys Asp Arg Gln Gly His Tyr

```
                50                  55                  60
Gly Tyr Tyr Thr Asn Ile Ala His Phe Tyr Asn Trp Ile Gln Asn Val
 65                  70                  75                  80

Thr Asn Val Leu Asn Asn
                 85

<210> SEQ ID NO 14
<211> LENGTH: 598
<212> TYPE: PRT
<213> ORGANISM: Crassostrea gigas

<400> SEQUENCE: 14

Met Glu Ser Tyr Glu Asn Cys Ser Phe Asp Ser Leu Thr Val Phe Ala
 1               5                  10                  15

Thr Glu His Leu Glu Ser Thr Gln Ile Gly Arg Val Cys Gly Leu Pro
                20                  25                  30

Glu Glu Ser Arg Val Phe Glu Ser Ala Ser Glu Ser Ile Arg Leu Glu
            35                  40                  45

Phe Arg Ser Asp Ser Met Val His Trp Arg Gly Tyr Gln Ala Thr Phe
        50                  55                  60

Gln Leu Ile Pro Lys Lys Ala Cys Tyr Pro Ser Cys Leu Pro Gly Thr
 65                  70                  75                  80

Val Cys Val Asn Gln Gly Gly Ser Leu Thr Cys Val Ala Gly Leu Lys
                85                  90                  95

Cys Pro Val Asp Ile Cys Asn His Gly Asp Cys Val Gln Asn His His
            100                 105                 110

Gly Glu Phe Lys Cys Phe Cys His Gly Tyr Thr Gly Ala Phe Cys
        115                 120                 125

Arg Ile Lys Gly Asn Ser Glu Lys Asn Ser Thr Arg Met Ile Met Leu
130                 135                 140

Lys Ser Pro Ser Asp Leu Ala Val Phe Arg Gly Glu Arg Glu Ile Ile
145                 150                 155                 160

Glu Cys Asn Ser Asn Asp Pro Ser Ala Gln Tyr Ile Trp Leu Phe Lys
                165                 170                 175

Gly Met Leu Leu Gln Ser Asp Ser Ala His Ile Thr Val Leu Pro Gly
            180                 185                 190

Gly Ile Leu Asp Ile Arg Asp Phe Asn Glu Glu Leu Gln Gly Thr Tyr
        195                 200                 205

Lys Cys Ile Ala Ser Thr Ala Thr Asp Phe Ala Glu Thr Glu Phe Arg
    210                 215                 220

Leu Ser Leu Lys Glu Lys Cys Phe Leu Val Val Glu Thr Pro Pro Glu
225                 230                 235                 240

Asp Thr Ala Val Glu Ser Gly Ser Thr Val Leu Leu Ser Cys Phe Val
                245                 250                 255

Pro Asp Ala Lys Lys Ile Thr Trp Phe Lys Asp Gly Lys Gln Leu Leu
            260                 265                 270

Ser Thr Gln His Thr Ile Leu Ala Ser Gly Phe Tyr Leu Lys Ile Asp
        275                 280                 285

Ser Val Lys His Asn Asp Val Gly Asn Tyr Ser Cys Gln Ala Glu Gly
    290                 295                 300

Glu Gly Gly Cys Ser Ala Gln Arg Ser Ala Met Leu Thr Ile Val Glu
305                 310                 315                 320

Glu Thr Lys Met Asp Gln Glu Asp Lys Cys Gly Val Pro Ala Leu Ser
                325                 330                 335
```

```
Gly Met Val Pro Gln Leu Ser Ser Arg Ile Ser Gly Gly Arg Ala Val
            340                 345                 350

Thr Met Glu Thr Thr Ala Trp His Val Ile Leu Arg Glu Asn Glu Lys
            355                 360                 365

Glu Lys Thr Phe Cys Gly Gly Thr Leu Ile Ser Asn Thr Trp Val Val
            370                 375                 380

Thr Ala Ala His Cys Phe Ala His Tyr Pro Asn Glu Phe Lys Arg Pro
385                 390                 395                 400

Phe Val Lys Ser Asn Ile Asp Val Ile Leu Gly Thr Asn Gln Cys Lys
            405                 410                 415

Gly Lys Gly Gly Val Lys Arg Lys Ile Lys Arg Tyr Ile Ile His Pro
            420                 425                 430

Lys Phe Ala Glu Arg Ser Ser Tyr Asp Asn Asp Ile Ala Leu Ile Glu
            435                 440                 445

Met Asp Glu Ala Val Asn Phe Thr Asp Lys Ile Gln Pro Leu Cys Leu
            450                 455                 460

Lys Pro Thr Ser Ile Ile Asp Asp Leu Phe Leu Ser Arg Arg Gly Gly
465                 470                 475                 480

Arg Arg Val Gly Arg Val Ile Gly Cys Gly Gln Arg Tyr Glu Asn Ile
            485                 490                 495

Glu Asp Thr Pro Asp Leu Ile His Asp Val Tyr Val Pro Ile Ile Ser
            500                 505                 510

Arg Glu Ile Cys Thr Gly Ala Asn Ile Gly Ser Gly Asn Phe Thr Asp
            515                 520                 525

Thr Met Phe Cys Ala Gly Tyr Glu Arg Ala Leu Phe Gly Asp Ala Cys
            530                 535                 540

Tyr Gly Asp Ser Gly Gly Ser Leu Ser Val Gln Leu Ser Asp Ser His
545                 550                 555                 560

Pro Trp Val Leu Val Gly Val Val Ser Trp Gly Val Gly Cys Asp Arg
            565                 570                 575

Pro Gly Gln Tyr Gly Tyr Tyr Thr Asn Val Gly Lys Phe Tyr Asn Trp
            580                 585                 590

Ile Gln Glu Asn Val Asn
            595

<210> SEQ ID NO 15
<211> LENGTH: 923
<212> TYPE: PRT
<213> ORGANISM: Euprymna scolopes

<400> SEQUENCE: 15

Met Ala Arg Arg His Phe Leu Asn Asn Thr Ala Thr Ile Ala Thr Ala
1               5                   10                  15

Tyr Leu Phe Leu Met Asn Phe Thr Tyr Ala Trp Glu Asp Ser Val Arg
            20                  25                  30

Cys Gly Glu Asp Phe Thr Glu Lys Ala Gly Ala Ile Lys Ser Pro Asn
            35                  40                  45

Tyr Pro Asp Pro Tyr Pro Ala Phe Ser Asp Cys Met Trp Lys Ile Lys
            50                  55                  60

Ala Pro Thr Gly Tyr Arg Ile Ser Ile His Ser Thr Ala Leu Arg Met
65                  70                  75                  80

Glu Gly Gly Gly Cys Asp Phe Asp Tyr Leu Lys Ile Thr Asp Ser Asp
            85                  90                  95

Tyr Ala Gln Asp Ser Gln Lys Gln Ser Ser Glu Val Phe Cys Gly Gln
            100                 105                 110
```

-continued

```
Lys Ser Val Asp Tyr Gln Ser Leu Thr Asn Glu Val Thr Leu His Phe
    115                 120                 125

Ile Ser Asp Ala Thr Glu Ser Tyr Tyr Gly Phe Asn Leu Tyr Tyr Thr
130                 135                 140

Phe Lys His Ala Ser Met Leu Lys Ser Ala Met Asp Tyr Cys Asn Met
145                 150                 155                 160

Thr Asn Ile Asn Thr Pro Gly Phe Leu Ser Ser Pro Gly Tyr Pro Lys
                165                 170                 175

Pro Tyr Gly Gly His Thr Asp Cys Phe Tyr His Leu Lys Ala Pro Ser
            180                 185                 190

Asp Gln Lys Ile Gln Leu Glu Phe Leu Val Phe Asp Leu Gln Tyr Asn
        195                 200                 205

Thr Lys Cys Arg Phe Asn Tyr Leu Gln Val Phe Asp Gly Pro Asp Met
    210                 215                 220

Thr Tyr Pro His Ser Glu Arg Phe Cys Gly Lys Gln Asp Ile Gly Phe
225                 230                 235                 240

Tyr Tyr Ser His Gly Ser Glu Leu Leu Ile Arg Phe Val Ser Thr Ser
                245                 250                 255

Ser Tyr Tyr Thr Gly Ala Gly Phe Asn Val His Phe Thr Ala His Thr
            260                 265                 270

Ser Phe Thr Met Asp Asp Ser Asn Arg Ser Gly Ser Asp Asp Ile Ile
        275                 280                 285

Glu Pro Thr Ala Glu Cys Lys Lys Ile Ile Glu Arg Lys Gly Val Lys
    290                 295                 300

Leu His Ser Pro Gly Tyr Pro Glu Val Tyr Pro Ser Asn Thr Gln Cys
305                 310                 315                 320

Thr Tyr Ile Ile Arg Ser Pro Pro Glu Glu Thr Val Thr Leu Thr Phe
                325                 330                 335

His Lys Phe Lys Leu Glu Asp Asp Pro Asp Cys Arg Tyr Asp Tyr Val
            340                 345                 350

Lys Ile Lys Asp Gly Glu Ser Ala Ala Ala Asp Val Leu Asp Lys Leu
        355                 360                 365

Cys Gly Thr His Asn Asn Lys Thr Tyr Thr Ser Thr Gly Arg Ser Leu
    370                 375                 380

Arg Leu Asp Phe Ile Ser Asp Ala Glu Val Ser Tyr Met Gly Phe Ser
385                 390                 395                 400

Ala Ser Tyr Thr Phe Ser Asn Cys Pro Lys Arg Cys Arg Asn Gly Gly
                405                 410                 415

Thr Cys Phe Asn Asn Arg Cys Lys Cys Pro His Gly Phe Thr Gly Pro
            420                 425                 430

Gln Cys Glu Tyr His Glu Ser Cys Ser Asp Arg Pro Cys Leu Asn Asn
        435                 440                 445

Ala Thr Cys Ser Glu Arg Arg Val Gly Tyr Lys Cys Tyr Cys Thr Asp
    450                 455                 460

Gly Tyr Thr Gly Tyr Asn Cys Glu Lys Lys Tyr Val Val Lys Leu
465                 470                 475                 480

Val Gly Gln Ala Arg Val Glu Arg Leu Thr Asn Val Glu Phe Lys Cys
                485                 490                 495

Leu Leu Asn Gly Glu Lys Ala Arg Asn Val Asn Trp Phe Phe Asn Gly
            500                 505                 510

Asp Lys Leu Lys Gly Gln Arg Ser Gly Arg Val Gln Thr Asp Glu Asn
        515                 520                 525
```

Val Leu Tyr Ile His Lys Ala Thr Glu Glu Asp Gly Glu Tyr Met
530                     535                 540

Cys Ala Val Phe Ile Lys Lys Thr Ala Tyr Tyr Asn Ile Lys Gln Leu
545                 550                 555                 560

Val Val Asn Ala Arg Cys Asn Leu His Val Gly Lys Ala Val Asn Gln
            565                 570                 575

Thr Ala Ser Ala Asn Gln Lys Thr Arg Leu Phe Cys Pro Ile Lys Val
            580                 585                 590

Tyr Gln Gly Ser Ser Val Ile Trp Lys Lys Asn Gly Tyr Pro Leu Lys
        595                 600                 605

Leu Gly Lys Arg Lys Ser Ala Ser Gly Arg Thr Val Lys Phe Arg Asn
610                 615                 620

Val Ile Ala Val Asp Ala Gly Lys Tyr Thr Cys Ile Ala Val Gly Pro
625                 630                 635                 640

Thr Gly Cys Ser Ala Lys Ala Asp Val Trp Leu Thr Tyr Gln Gly Arg
            645                 650                 655

Glu Leu Pro Gln Glu Cys Gly His Asn Ser Phe Asn His His Asp His
            660                 665                 670

Ser Ile Leu Ala Lys Ile Gln Ser Gly His Pro Ala Ala Phe Gly Ser
            675                 680                 685

Ala Pro Trp Phe Val Asn Phe Val Lys Val Ala Asp Lys Asn Ser Phe
690                 695                 700

Cys Gly Gly Thr Leu Ile Ser Arg Asn His Thr Val Thr Ala Ala His
705                 710                 715                 720

Cys Ile Ser Val Phe Pro Gly Val Phe Asn Asn Thr Asn Val His Ile
            725                 730                 735

Tyr Leu Gly Thr Gln Asn Cys Ser Gly Val Gly Gly Leu Gln Val Gln
            740                 745                 750

Met Lys Ser Ile Thr Leu His Pro Ser Phe Asn Lys Ser Ser Val Phe
            755                 760                 765

Asp Ser Asp Ile Ala Ile Val Glu Phe Tyr Glu Lys Leu His Phe Ser
770                 775                 780

Lys Asn Ile Arg Pro Leu Cys Leu Val Asp Lys Ala Val Ile Glu Glu
785                 790                 795                 800

Val Ala Phe Tyr Ser Gly Val Tyr Gly Thr Val Val Gly Cys Gly Leu
            805                 810                 815

Thr Ser Asn Gly Ile Tyr Pro Ser Tyr Leu Asn Glu Val Lys Val Pro
            820                 825                 830

Tyr Val Ser Asn Glu Asn Cys Arg Thr Thr Leu Gln Ser Gly His Asn
            835                 840                 845

Leu Thr Glu Asn Met Phe Cys Ala Gly Ser Arg Gln Ala His Arg Gly
850                 855                 860

Asp Ser Cys Tyr Gly Asp Ser Gly Gly Pro Tyr Ala Val Gln Ser Pro
865                 870                 875                 880

Ser Ser Asn Arg Trp Met Leu Val Gly Ile Val Ser Trp Gly Tyr Lys
            885                 890                 895

Cys Asp Gln Arg Asp Ala Tyr Gly Phe Tyr Thr Asn Val Gly Gln Phe
            900                 905                 910

Tyr Asp Trp Ile Met Ser Val Ile Ser Lys Thr
            915                 920

<210> SEQ ID NO 16
<211> LENGTH: 922
<212> TYPE: PRT

<213> ORGANISM: Octopus vulgaris

<400> SEQUENCE: 16

```
Met Ala Pro Tyr Thr Thr Leu Gly Phe Leu Lys Arg Ala Val Ala Leu
1               5                   10                  15

Leu Leu Leu Tyr Val Thr Tyr Val Lys Cys Phe Ala Pro Glu Val Lys
            20                  25                  30

Cys Gly Gly Arg Ile Arg Glu Thr Ala Gly Ser Ile Ile Ser Pro Asn
        35                  40                  45

Tyr Pro Asp Asp Tyr Pro Pro Asn Ala Asp Cys Val Trp Ile Ile His
    50                  55                  60

Val Pro Lys Pro Phe Phe Val Ile Ile His Ser Thr Phe Phe Arg Leu
65                  70                  75                  80

Glu Asn Asp Cys Asn Phe Asp Gln Leu Val Ile Glu Asp Tyr Gly His
                85                  90                  95

Thr Tyr Asn Ser Lys Ser Gly His Lys Gln Thr Phe Cys Gly Arg Met
            100                 105                 110

Phe Val Tyr Phe Lys Ser Val Thr Asn Lys Val Arg Ile Thr Phe Lys
        115                 120                 125

Ser Asp Phe Gly Thr Asn Tyr Lys Gly Phe Asn Leu Lys Phe Tyr Ser
    130                 135                 140

Met Asp Asn Ser Phe Gly Ser Gly Pro Val Asp Trp Cys Asn Gln Thr
145                 150                 155                 160

Arg Ile Asp Gly Pro Gly Phe Leu Thr Ser Pro Gly Tyr Pro Thr Gln
                165                 170                 175

His Gln Phe Ser Gly Asp Cys Phe Tyr His Ile Lys Ala Pro Ile Gly
            180                 185                 190

Lys Arg Ile Lys Leu Glu Phe Leu Asp Phe Asp Leu Glu Glu Asn Thr
        195                 200                 205

Arg Cys Ala Tyr Asn Tyr Leu Gln Ile Val Asp Gly Pro Asp Leu Tyr
    210                 215                 220

Cys Pro Ser Ile Gly Arg Tyr Cys Gly Asn Gln Val Leu Ser Phe Ile
225                 230                 235                 240

Tyr Ser Ser Gly Ser Asp Leu Tyr Leu Arg Phe Ser Ser Ile Ser Gly
                245                 250                 255

Ile Tyr Thr Ser Thr Gly Phe Leu Ala Gln Phe Ser Phe His Thr Ser
            260                 265                 270

Thr Val Thr Asp His Thr Asn Gln Ser Gly Ser Asp Asp Tyr Leu Glu
        275                 280                 285

Lys Ala Leu Asp Cys Asn Gln Ile Ile Glu Glu Lys Ile Val Lys Ile
    290                 295                 300

Gln Ser Pro Gly Tyr Pro Glu Ser Tyr Pro Ala Asn Ala Arg Cys Val
305                 310                 315                 320

Tyr Ile Ile Arg Ser Pro Val Asp Glu Thr Val Thr Leu Thr Phe His
                325                 330                 335

Lys Met Val Leu Glu Asp Ser Glu Asn Cys Asp Leu Asp Tyr Val Lys
            340                 345                 350

Val Lys Asp Gly Glu Thr Ala Ala Ala Thr Val Leu Asp Lys Leu Cys
        355                 360                 365

Arg Asn Gln Asn Lys Ser Tyr Thr Ser Ser Gly Arg Ser Leu Arg Leu
    370                 375                 380

Asp Phe Val Thr Asn Asp Glu Ile Ser Tyr Met Gly Phe Thr Ala Thr
385                 390                 395                 400
```

```
Tyr Thr Phe Ser Asn Cys Pro Leu Arg Cys Arg Asn Gly Gly Val Cys
            405                 410                 415

Glu Asn His Arg Cys Ile Cys Pro His Gly Phe Gln Gly Arg Gln Cys
        420                 425                 430

Asp Leu Pro Val Gly Cys Asn Glu Glu Pro Cys Lys Asn Gly Ala Thr
    435                 440                 445

Cys Arg Glu Arg Lys Ile Gly Tyr Ile Cys Leu Cys Pro Glu Gly Tyr
450                 455                 460

Thr Gly Tyr Asn Cys Glu Lys Leu Lys Tyr Val Glu Ile Glu Gly
465                 470                 475                 480

Lys Ser Tyr Val Lys Arg Leu Gly Asn Ile Val Tyr Thr Cys Arg Leu
                485                 490                 495

Asn Gly Lys Ile Pro Asp Lys Val Phe Trp Phe Arg Asn Gly Asp Leu
            500                 505                 510

Leu Gln Gly Asn Val Asn Glu Arg Ile Glu Ala Thr Asp Val Leu Tyr
        515                 520                 525

Ile Glu Arg Val Thr Glu Leu Asp Glu Ala Gln Tyr Met Cys Val Val
    530                 535                 540

Tyr Lys Asp Leu Met Ala Tyr Phe Asp Thr Lys Asn Leu Thr Ile Glu
545                 550                 555                 560

Pro Thr Cys His Leu Gln Thr Thr Gln Pro Val Asn Arg Ser Val Ile
                565                 570                 575

His Ser Gly Asn Val Ala Leu Arg Cys Pro Val Ile Ala Thr Lys Gly
            580                 585                 590

Val Arg Phe Thr Trp Gln Lys Asp Gly His Pro Leu Lys Met Asn Lys
        595                 600                 605

Arg Arg Tyr Ile Tyr Ser Asn Ser Leu Ile Phe Lys Asp Val Glu Glu
    610                 615                 620

Val Asp Asn Gly Thr Tyr Lys Cys Leu Ala Val Gly Pro Thr Glu Cys
625                 630                 635                 640

Ser Ala Ala Glu Met Ser Leu Thr Val Asn Phe Lys Arg Asn Pro
                645                 650                 655

Asn Lys Val Cys Gly Lys Asn Ser Ile Thr Lys Asn Ser Glu Asn Ile
            660                 665                 670

Glu Ala Lys Ile Lys Ser Gly Tyr Pro Ala Ala Arg Gly Ser Ala Pro
        675                 680                 685

Trp Phe Val Leu Phe Val Arg Ser Ala Thr Ser His Ser Phe Cys Gly
    690                 695                 700

Gly Thr Leu Val Gly Asn Lys His Ile Val Thr Ala Ala His Cys Ile
705                 710                 715                 720

Arg Ser Phe Gln Asn Phe Asn Asn His Asn Val His Val Tyr Val Gly
                725                 730                 735

Thr Gln Asn Cys Ser Gly His Gly Gly Ile Arg Val Gln Met Lys His
            740                 745                 750

Trp Ile Val His Pro Ala Phe Asn Glu Thr Thr Phe Asp Ser Asp Ile
        755                 760                 765

Ala Val Ile Val Leu Lys Glu Thr Leu Asp Phe Thr Pro Tyr Val His
    770                 775                 780

Pro Leu Cys Leu Val Asn Glu Val Ile Gly Glu Ser Phe Tyr Ser
785                 790                 795                 800

Gly Phe Tyr Gly Thr Val Val Gly Cys Gly Glu Thr Ala Phe Gly Tyr
                805                 810                 815

Asn Ser Tyr Pro Arg His Leu His Glu Val Lys Leu Pro Tyr Val Ser
```

```
                    820                 825                 830
Asp Asn Gln Cys Arg Lys Arg Leu Ala Lys Gly His Asn Ile Thr Lys
                835                 840                 845

Asn Met Phe Cys Ala Gly Phe Tyr Arg Ala Tyr Gln Gly Asp Ser Cys
            850                 855                 860

Lys Gly Asp Ser Gly Gly Pro Tyr Thr Ile Leu Pro Gln Ser Lys
865                 870                 875                 880

Arg Trp Ile Leu Val Gly Ile Val Ser Trp Gly Tyr Asn Cys Asp Arg
                885                 890                 895

Ser Asn Ser Ile Gly Val Tyr Thr Asn Val Gly Gln Phe Tyr Lys Trp
            900                 905                 910

Leu Thr Lys Thr Val Ser Val Arg His His
                915                 920

<210> SEQ ID NO 17
<211> LENGTH: 604
<212> TYPE: PRT
<213> ORGANISM: Mus musculus

<400> SEQUENCE: 17

Met Pro Leu Ala Met Leu Leu Leu Leu Leu Leu Leu Ser Pro Asp
1               5                   10                  15

Ser Gln Thr Ala His Gly His Pro Leu Tyr Thr Arg Leu Ser Pro Gly
                20                  25                  30

Ala Leu Gln Val Leu Ser Ala Gln Gly Thr Gln Ala Leu Gln Ala Ala
            35                  40                  45

Gln Arg Ser Ala Gln Trp Ala Ile Lys Arg Val Leu Met Glu Ile Gln
        50                  55                  60

His Arg Leu His Glu Cys Gln Gly Pro Gly Arg Pro Arg Pro Gln Ala
65                  70                  75                  80

Pro Leu Leu Gln Asp Pro Pro Glu Pro Val Gln Cys Gly Glu Arg His
                85                  90                  95

Gln Gly Val Ala Asn Thr Thr Arg Ala His Gly Arg Ile Val Gly Gly
            100                 105                 110

Ser Thr Ala Pro Ser Gly Ala Trp Pro Trp Leu Val Arg Leu Gln Leu
        115                 120                 125

Gly Gly Leu Pro Leu Cys Gly Gly Val Leu Val Ala Ala Ser Trp Val
130                 135                 140

Leu Thr Ala Ala His Cys Phe Ala Gly Ala Ser Asn Glu Leu Leu Trp
145                 150                 155                 160

Thr Val Met Leu Ala Glu Gly Pro Gln Gly Gln Ala Glu Val
                165                 170                 175

Gln Val Asn Arg Ile Leu Pro His Pro Lys Phe Asp Pro Gln Thr Phe
            180                 185                 190

His Asn Asp Leu Ala Leu Val Gln Leu Trp Thr Pro Val Ser Pro Glu
        195                 200                 205

Gly Pro Ala Arg Pro Ile Cys Leu Pro Gln Gly Ser Arg Glu Pro Pro
210                 215                 220

Ala Gly Thr Pro Cys Ala Ile Ala Gly Trp Gly Ala Leu Phe Glu Asp
225                 230                 235                 240

Gly Pro Glu Ser Glu Ala Val Arg Glu Ala Arg Val Pro Leu Leu Ser
                245                 250                 255

Ala Asp Thr Cys Gln Lys Val Leu Gly Pro Gly Leu Arg Pro Ser Thr
            260                 265                 270
```

```
Met Leu Cys Ala Gly Tyr Leu Ala Gly Gly Ile Asp Ser Cys Gln Gly
            275                 280                 285

Asp Ser Gly Gly Pro Leu Thr Cys Ser Glu Pro Gly Pro Arg Pro Arg
        290                 295                 300

Glu Val Leu Phe Gly Val Thr Ser Trp Gly Asp Gly Cys Gly Glu Pro
305                 310                 315                 320

Gly Lys Pro Gly Val Tyr Thr Arg Val Thr Val Phe Lys Asp Trp Leu
                325                 330                 335

Gln Glu Gln Met Ser Ala Gly Pro Ser Thr Arg Glu Pro Ser Cys Arg
            340                 345                 350

Glu Leu Leu Asn Trp Asn Ala Arg Glu Glu Pro Phe Thr Asp Ala
        355                 360                 365

Pro Gly Leu Cys Ala Phe Tyr Ala Arg Gln Cys Leu Gly Ser Glu Ser
    370                 375                 380

Ser Cys Ala Arg Leu Ala Leu Gln Gln Cys Leu Gln Arg Arg Arg
385                 390                 395                 400

Cys Glu Leu Arg Ser Leu Ala His Thr Leu Leu Gly Leu Leu Arg Gly
                405                 410                 415

Ala Gln Glu Leu Leu Gly Pro Arg Pro Gly Leu Arg Arg Gly Val Ser
            420                 425                 430

Ala Pro Ala Arg Ser Ala Pro Ser Leu Gln Glu Leu Pro Gly His Asn
        435                 440                 445

Pro Arg Glu Gln Arg Leu Tyr Ser Gly Ser Arg Ile Ala Gly Thr Trp
    450                 455                 460

Leu Gln Lys Pro Lys Pro Glu Arg Arg Pro Glu Thr Lys Gly Cys Pro
465                 470                 475                 480

Gly Leu Glu Pro Leu Gln Gln Lys Leu Ala Ala Ile Gln Arg Ala His
                485                 490                 495

Ala Trp Ile Leu Gln Ile Pro Ala Glu His Leu Ala Met Asn Phe His
            500                 505                 510

Glu Val Leu Ala Asp Leu Gly Ser Lys Thr Leu Thr Gly Leu Phe Arg
        515                 520                 525

Ala Trp Val Arg Ala Gly Leu Gly Asp Gln Arg Val Val Phe Ser Gly
    530                 535                 540

Leu Val Gly Leu Glu Pro Ser Thr Leu Ala His Ser Leu Pro Arg Leu
545                 550                 555                 560

Leu Val Gln Ala Leu Lys Ala Phe Arg Ser Ala Ser Leu Thr Glu Gly
                565                 570                 575

Glu Pro Gln Ala Pro Trp Ile Gly Ala Asp Gln Gly Gln Arg Leu Gly
            580                 585                 590

Lys Glu Arg Gln Gly Gln Leu Gln Pro Pro Val Pro
        595                 600

<210> SEQ ID NO 18
<211> LENGTH: 250
<212> TYPE: PRT
<213> ORGANISM: Homo sapiens

<400> SEQUENCE: 18

Met Arg Ile Leu Gln Leu Ile Leu Leu Ala Leu Ala Thr Gly Leu Val
1               5                   10                  15

Gly Gly Glu Thr Arg Ile Ile Lys Gly Phe Glu Cys Lys Pro His Ser
            20                  25                  30

Gln Pro Trp Gln Ala Ala Leu Phe Glu Lys Thr Arg Leu Leu Cys Gly
        35                  40                  45
```

```
Ala Thr Leu Ile Ala Pro Arg Trp Leu Leu Thr Ala Ala His Cys Leu
 50                  55                  60

Lys Pro Arg Tyr Ile Val His Leu Gly Gln His Asn Leu Gln Lys Glu
 65                  70                  75                  80

Glu Gly Cys Glu Gln Thr Arg Thr Ala Thr Glu Ser Phe Pro His Pro
                 85                  90                  95

Gly Phe Asn Asn Ser Leu Pro Asn Lys Asp His Arg Asn Asp Ile Met
                100                 105                 110

Leu Val Lys Met Ala Ser Pro Val Ser Ile Thr Trp Ala Val Arg Pro
            115                 120                 125

Leu Thr Leu Ser Ser Arg Cys Val Thr Ala Gly Thr Ser Cys Leu Ile
        130                 135                 140

Ser Gly Trp Gly Ser Thr Ser Ser Pro Gln Leu Arg Leu Pro His Thr
145                 150                 155                 160

Leu Arg Cys Ala Asn Ile Thr Ile Ile Glu His Gln Lys Cys Glu Asn
                165                 170                 175

Ala Tyr Pro Gly Asn Ile Thr Asp Thr Met Val Cys Ala Ser Val Gln
                180                 185                 190

Glu Gly Gly Lys Asp Ser Cys Gln Gly Asp Ser Gly Gly Pro Leu Val
            195                 200                 205

Cys Asn Gln Ser Leu Gln Gly Ile Ile Ser Trp Gly Gln Asp Pro Cys
210                 215                 220

Ala Ile Thr Arg Lys Pro Gly Val Tyr Thr Lys Val Cys Lys Tyr Val
225                 230                 235                 240

Asp Trp Ile Gln Glu Thr Met Lys Asn Asn
                245                 250

<210> SEQ ID NO 19
<211> LENGTH: 130
<212> TYPE: PRT
<213> ORGANISM: Geospiza fortis

<400> SEQUENCE: 19

Arg Ile Gln Val Gln Leu Gly Lys His Asn Leu Glu Leu Thr Glu Ser
 1                    5                  10                  15

Thr Gln Gln Phe Ile Asn Ser Ala Lys Val Ile Arg His Ser Gly Phe
                 20                  25                  30

Ser Ser Tyr Thr Leu Asp Asn Asp Ile Met Leu Ile Lys Leu Ala Thr
             35                  40                  45

Pro Ala Thr Leu Ser Lys Ala Val Gln Thr Val Pro Leu Pro Thr Ser
 50                  55                  60

Cys Val Ala Ala Gly Thr Thr Cys Leu Ile Ser Gly Trp Gly Asn Thr
 65                  70                  75                  80

Leu Ser Ser Gly Ser Asn Tyr Pro Asp Gln Leu Gln Cys Leu Lys Ala
                 85                  90                  95

Pro Val Leu Thr Ala Glu Gln Cys Ser Asp Ala Tyr Pro Gly Gln Ile
            100                 105                 110

Thr Asn Asn Met Met Cys Val Gly Tyr Val Glu Gly Gly Lys Asp Ser
            115                 120                 125

Cys Gln
    130

<210> SEQ ID NO 20
<211> LENGTH: 249
<212> TYPE: PRT
```

<213> ORGANISM: Zonotrichia albicollis

<400> SEQUENCE: 20

Met Lys Cys Leu Leu Leu Ala Phe Ile Gly Val Ala Val Ala Phe
1               5                   10                  15

Pro Thr Phe Ala Glu Asp Asp Asp Lys Ile Val Gly Gly Tyr Thr
                20                  25                  30

Cys Ala Glu Asn Ser Val Pro Tyr Gln Val Ser Leu Asn Ser Gly Tyr
            35                  40                  45

His Phe Cys Gly Gly Ser Leu Ile Ser Ser Gln Trp Val Val Ser Ala
        50                  55                  60

Ala His Cys Tyr Lys Ser Arg Ile Gln Val Leu Gly Lys His Asn
65                  70                  75                  80

Leu Gly Leu Thr Glu Ser Thr Gln Gln Phe Ile Asn Ser Ala Lys Val
                85                  90                  95

Ile Arg His Ser Gly Tyr Ser Ser Tyr Thr Leu Asp Asn Asp Ile Met
            100                 105                 110

Leu Ile Lys Leu Ala Thr Pro Ala Thr Leu Ser Lys Ala Ile Gln Thr
        115                 120                 125

Ile Pro Leu Pro Thr Ser Cys Val Ala Ala Gly Thr Thr Cys Leu Ile
    130                 135                 140

Ser Gly Trp Gly Asn Thr Leu Ser Ser Gly Ser Asn Tyr Pro Asp Glu
145                 150                 155                 160

Leu Gln Cys Leu Lys Ala Pro Val Leu Thr Asp Glu Gln Cys Ser Asp
                165                 170                 175

Ala Tyr Pro Gly Gln Ile Thr Lys Asn Met Ile Cys Val Gly Tyr Leu
            180                 185                 190

Glu Gly Gly Lys Asp Ser Cys Gln Gly Asp Ser Gly Gly Pro Val Val
        195                 200                 205

Cys Asn Gly Glu Leu Gln Gly Ile Val Ser Trp Gly Tyr Gly Cys Ala
    210                 215                 220

Gln Arg Gly Leu Pro Gly Val Tyr Thr Lys Val Cys Asn Tyr Val Ser
225                 230                 235                 240

Trp Ile Gln Ser Thr Ile Ala Ser Asn
                245

<210> SEQ ID NO 21
<211> LENGTH: 247
<212> TYPE: PRT
<213> ORGANISM: Oryzias latipes

<400> SEQUENCE: 21

Met Lys Leu Leu Leu Phe Leu Ile Leu Phe Glu Gly Ala Val Ala Leu
1               5                   10                  15

Gln Glu Asp Glu Lys Ile Val Gly Gly Phe Glu Cys Gln Lys Asn Ser
                20                  25                  30

Val Pro Tyr Gln Val Ser Leu Phe Thr Gly Tyr Asn Tyr Cys Gly Gly
            35                  40                  45

Thr Leu Leu Ser Glu Gln Trp Val Leu Ser Ala Ala His Cys Glu Pro
        50                  55                  60

Lys Ser Asn Leu Glu Val Arg Leu Gly Glu His Asp Ile Trp Glu Pro
65                  70                  75                  80

Glu Gly Thr Glu Gln His Ile Met Ser Ala Lys Phe Ile Arg His Pro
                85                  90                  95

Asn Tyr Asp Pro Arg Thr Gln Asp Asn Asp Ile Met Leu Ile Lys Leu

```
                100             105             110
Ser Glu Pro Ala Thr Leu Asn Ser Phe Val Arg Pro Ala Val Leu Pro
            115                 120                 125

Ser Lys Cys Glu Asn Asp Gly Thr Met Cys Arg Ile Ser Gly Trp Gly
            130                 135                 140

Asn Ile Arg Ser Ser Asp Glu Gly Ser Arg Tyr Pro Asp Lys Leu Gln
145                 150                 155                 160

Cys Leu Asp Ala Pro Leu Leu Ser Asp Glu Thr Cys Phe Asn Ala Tyr
                165                 170                 175

Pro Phe Gln Ile Thr Glu Asn Met Ile Cys Ala Gly Tyr Leu Glu Gly
            180                 185                 190

Gly Lys Asp Ser Cys Gln Gly Asp Ser Gly Gly Pro Met Thr Cys Asp
            195                 200                 205

Gly Glu Leu Gln Gly Val Val Ser Trp Gly His Gly Cys Ala Met Lys
            210                 215                 220

Asn Lys Pro Gly Val Tyr Thr Lys Val Cys Asn Tyr Val Ser Trp Ile
225                 230                 235                 240

Lys Glu Thr Met Ala Ser Asp
                245

<210> SEQ ID NO 22
<211> LENGTH: 251
<212> TYPE: PRT
<213> ORGANISM: Fundulus heteroclitus

<400> SEQUENCE: 22

Met Gln Leu Ala Pro Leu Cys Phe Leu Leu Leu Pro Leu Ile Val
1               5                   10                  15

Ala Asn Leu Thr Val Glu Asn Asp Lys Arg Ile Ile Gly Gly Thr Val
            20                  25                  30

Val Glu Pro Tyr Ser Ile Lys Tyr Gln Ala Ser Leu Leu Tyr Arg Gly
            35                  40                  45

Ser His Phe Cys Gly Gly Thr Leu Val His Pro Gln Trp Val Val Ser
    50                  55                  60

Ala Ala His Cys Trp Arg Pro Asn Gln Leu Met Gln Val Val Leu Gly
65                  70                  75                  80

Glu His Asn Ile Lys Glu Lys Glu Gly Phe Glu Gln Ile Phe Asp Ile
                85                  90                  95

Leu Leu Ile Ile Lys His Tyr Gln Phe Asn Tyr Trp Asn Leu Asp Asn
                100                 105                 110

Asp Ile Met Leu Leu Lys Leu Asp Arg Pro Ala Ile Ile Asn Asp Val
            115                 120                 125

Val Ser Pro Val Ile Leu Pro Arg Thr Gly Thr Leu Gln Ser Phe Ala
            130                 135                 140

Arg Cys Thr Val Ser Gly Trp Gly Val Thr Trp Val Tyr Gly Gln Ser
145                 150                 155                 160

Leu Ser Asp Gln Leu Met Ser Val Asp Val Asp Tyr Phe Ala Asp Cys
                165                 170                 175

Trp Tyr Tyr Tyr Tyr Phe Arg Ile Thr Asn Asn Met Ile Cys Ala Gly
                180                 185                 190

Ser Thr Ala Gly Gly Lys Asp Ser Cys Gln Gly Asp Ser Gly Gly Pro
            195                 200                 205

Leu Ile Cys Asn Gly Val Leu Glu Gly Ile Val Ser Trp Gly Ile Gly
            210                 215                 220
```

-continued

```
Cys Ala Tyr Ser Phe Tyr Pro Gly Val Tyr Ser Lys Val Arg Asn Tyr
225                 230             235                 240

Val Ser Trp Ile Asp Trp Ala Ile Gln Asn Ser
                245             250
```

GENE FOR TRYPSIN-LIKE SERINE PROTEASE, A PROTEIN ENCODED THEREBY AND USE THEREOF

CROSS REFERENCE TO RELATED APPLICATION

This application claims the priority of Chinese Patent Application No. 202010589361.X, entitled "Gene for trypsin-like serine protease, a protein encoded thereby and use thereof" filed with the China National Intellectual Property Administration on Jun. 24, 2020, the entire content of which is incorporated in this application by reference.

TECHNICAL FIELD

The invention belongs to the technical field of genetic engineering, and specifically relates to a gene for trypsin-like serine protease, a protein encoded thereby and use thereof.

BACKGROUND

In recent years, due to the serious pollution of the marine environment and the frequent occurrence of diseases in aquaculture animals, the abuse of traditional antibiotics has led to the problem of more and more serious drug resistance to pathogenic microorganisms, posing a huge threat to the health of aquaculture animals and humans, and there is an urgent need to develop new antibacterial drugs. However, the ocean is a gathering place for most abundant species in the world, and the discovery of antibacterial substances from marine invertebrates having great potential. In order to solve the problems of antibiotic abuse and drug resistance, the inventors explore closely natural biological antibiotics to broaden the spectrum of antibiotics and improve the drug resistance.

SUMMARY

Based on the above reasons, the objective of the present disclosure is to provide a protein encoded by a gene for trypsin-like serine protease and its use. The protein encoded by the gene provided by the present disclosure is capable of inhibiting four microorganisms.

In order to achieve the above-mentioned objective of the invention, the following technical solution is provided.

The present disclosure provides a gene for trypsin-like serine protease, and the nucleotide sequence of the gene for trypsin-like serine protease is set forth in SEQ ID No. 1.

The present disclosure also provides the protein encoded by the gene for trypsin-like serine protease described in the above technical solution, this protein is short for PmTLS, and the amino acid sequence of the protein is set forth in SEQ ID No. 2.

The present disclosure further provides the use of the protein in the above technical solution in preparation of a medicament for inhibiting microbial.

In one embodiment of the present disclosure, the microorganism is one or more selected from the group consisting of *Pseudomonas aeruginosa, Aeromonas hydrophila, Vibrio parahaemolyticus,* and *Vibrio harveyi.*

The present disclosure provides a gene for trypsin-like serine protease, wherein the nucleotide sequence of the gene for trypsin-like serine protease is set forth in SEQ ID No. 1. The amino acid sequence of the protein encoded by the gene provided herein is set forth in SEQ ID No. 2. The protein is capable of inhibiting *P. aeruginosa, A. hydrophila, V. parahaemolyticus* and *V. harveyi.*

BRIEF DESCRIPTION OF THE DRAWINGS

FIG. 17A-FIG. 17K show the morphological changes of rPmTLS when acting on bacteria; FIG. 17A, FIG. 17E, and FIG. 17I represent the PBS control group for *P. aeruginosa, A. hydrophila,* and *V. parahaemolyticus,* respectively, FIG. 17B, FIG. 17C, and FIG. 17D represent the experimental group in which rPmTLS acts on *P. aeruginosa,* FIG. 17F, FIG. 17G, and FIG. 17H represent the experimental groups in which rPmTLS acts on *A. hydrophila,* and FIG. 17J and FIG. 17K represent the experimental groups in which rPmTLS acts on *V. parahaemolyticus.*

DETAILED DESCRIPTION OF THE EMBODIMENTS

Figure 1:
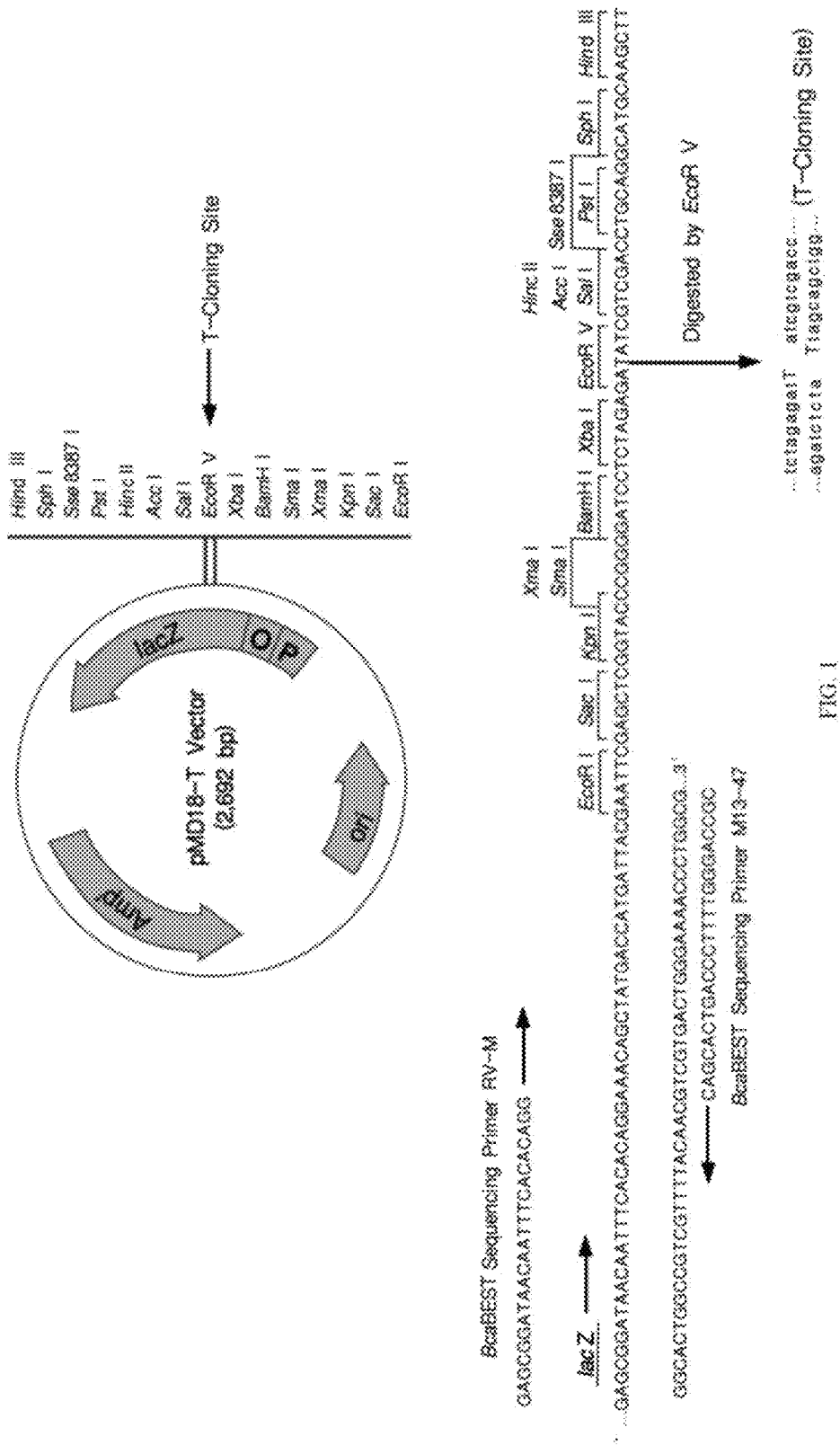
FIG. 1 is a schematic diagram of the cloning site of pMD19-T Vector.

The present disclosure provides a gene for trypsin-like serine protease, and the nucleotide sequence of the gene for trypsin-like serine protease is set forth in SEQ ID No. 1, specifically shown as follows:

ACATGGGCTAATAAATGGATCGTGACAGCCGCCCACTGTATCGTGCGTTT
TCCCGAGAAATTCCACGAATTGTTCCACCCCTCTAAGGTCACCCTTATTA
TTGGTACAGAGCAGTGTAGCGGATATGACGGCCAAATCGTGGACATCGAG
TCATATGTTGTGCATCCTAGATTTGCAGAAAGGGCTCCATACGACCATGA
TATAGCTTTGATAGAACTTCGTCAAGATTTAAACTTTACAGAACGTGTAC
AACCAATATGTCTCAAGCAGCCGGATTACGTGAATACTGCTTTCCTTCAT
CGCAAAGTCGGGCGTAAGGCAGGGAGGGTTGTAGGGTGTGGTCAATTGTA
TGAAAATGTAGATGCTATACCCACGGAGCTACATGACGTTTTCGTACCAA
CAGTGACTAGGGAGAAATG<u>TATGGAGGCGGACATAGGGCGAGGAAATTTC
ACTGACACTATGTTCTGCGCAGGGTATGACAGGGCTTTATTCGGAGATGC
TTGTTATGGTGATAGTGGTGGCTCTTTGGCGATGAATGACTCCCCATTTG
ACCCCTGGGTCCTTGTGGGCGTGGTGTCATGGGGAGTTGGGTGTGACCGA
CAAGGACATTATGGATACTATACAAATATAGCTCACTTTTATAACTGGAT
ACAAAATGTCACAAATGTTTTAAATAATTAGGATTGAAACAATAAAGAGA</u>
TATAGATCTTAATTTATACTATTGAGACACAATTAAAAAAAGTTTAACCC
TAAAAAAAAAAAAAAAAAAAAAAAAAAA.

The underline represents the open reading frame ORF of the gene for trypsin-like serine protease.

The present disclosure also provides the protein encoded by the gene for trypsin-like serine protease described in the above technical solution, the protein is short for PmTLS, which is the trypsin-like serine protease of *P.f. martensii*, and the amino acid sequence of the protein is as set forth in SEQ ID No. 2, which is shown in detail as follows:

MEADIGRGNFTDTMFCAGYDRALFGDACYGDSGGSLAMNDSPFDPWVLVG
VVSWGVGCDRQGHYGYYTNIAHFYNWIQNVTNVLNN.

The present disclosure further provides the use of the protein described in above technical solutions in preparation of microorganisms in the manufacture of a medicament for inhibiting a microorganism. In the present disclosure, the microorganism is preferably one or more selected from the group consisting of *P. aeruginosa, A. hydrophila, V. parahaemolyticus,* and *V. harveyi*.

The technical solutions provided by the present disclosure will be described in detail below in conjunction with the embodiments. However, these embodiments should not be understood as limiting the protection scope of the present disclosure.

EXAMPLE 1 a) Molecular Screening for Immune Effect of *P.f. martensii*

All amino acid sequences with previously verified antimicrobial activity were obtained from online antimicrobial peptide database (APD3, aps.unmc.edu/AP/main.php), PubMed ncbi.nlm.nih.gov/pubmed/) and the National Center for Biotechnology Information (NCBI) database (ncbi.nlm.nih.gov/). Subsequently, a local reference AMP database was constructed, and an alignment search was conducted based on the genome data of *P.f. martensii*. The gene sequence with highest alignment rate was collected, and then the online Blast in the NCBI database was used for analysis, and the type of the collected immune effector of the PmTLS gene was predicted.

b) Design of Related Primer for PmTLS Gene

Specific primers for TLS gene were designed using Primer Premier 5.0. The 5'-terminal and 3'-terminal specific primers were designed according to the principle of RACE amplification, and full-length of cDNA of the gene was obtained by alignment and splicing. The primer sequence is as follows.

TABLE 1

Primers

| Primer | Sequence (5'-3') | Sequence number | Use |
|---|---|---|---|
| PmTLS-3'-inner | TATGGAGGCGGACATAGGGCG | SEQ ID No. 3 | 3'-RACE |
| PmTLS-3'-outer | CATCGCAAAGTCGGGCGTAAG | SEQ ID No. 4 | 3'-RACE |
| PmTLS-5'-inner | TGTCCGCCTCCATACATTTCTCC | SEQ ID No. 5 | 5'-RACE |
| PmTLS-5'-outer | ATGACACCACGCCCACAAGG | SEQ ID No. 6 | 5'-RACE |
| M13-F | CGCCAGGGTTTTCCCAGTCACGAC | SEQ ID No. 7 | Colony PCR detection |
| M13-R | GAGCGGATAACAATTTCACACAGG | SEQ ID No. 8 | Colony PCR detection |
| PmTLS-RT-F | AGAAATGTATGGAGGCGGAC | SEQ ID No. 9 | Fluorescence quantification |

TABLE 1-continued

Primers

| Primer | Sequence (5'-3') | Sequence number | Use |
| --- | --- | --- | --- |
| PmTLS-RT-R | ACCATAACAAGCATCTCCGAAT | SEQ ID No. 10 | Fluorescence quantification |
| GAPDH-F | GCAGATGGTGCCGAGTATGT | SEQ ID No. 11 | Reference gene |
| GAPDH-R | CGTTGATTATCTTGGCGAGTG | SEQ ID No. 12 | Reference gene |

Total RNA Extraction

A whole tissue sample of *P.f. martensii* was obtained, Trizol was added and each tissue was ground, total RNA was extracted according to the principle of Trizol method.

RNA integrity and quality were detected using 1% agarose gel electrophoresis.

Concentration and purity of the total RNA were measured by using a micro-nucleic acid quantifier.

The obtained total RNA was stored in an ultra-low temperature refrigerator at −80° C. for later use.

Synthesis of the First Strand of cDNA

The required template was prepared according to the operation instruction of the Reverse Transcriptase M-MLV kit. The specific procedures are as follows.

Binding RNA to the primers: the PCR procedure is 70° C., 10 min, and placement on ice for 2 to 3 min. The sample system is as follows:

TABLE 2 sample system

| Reagent | Dose |
| --- | --- |
| Total RNA | 1 ng-1 µg |
| Oligo (dT) (50 uM) | 1 µL |
| RNase-free water | Make up to 8 µL |

(2) Adding the following reagents to the above RNA system:

TABLE 3

Reagents

| Reagent | Dose |
| --- | --- |
| 5 × M-MLV Buffer | 2.0 µL |
| dNTP Mixture (10 mM) | 0.5 µL |
| RNase Inhibitor | 0.25 µL |
| RTase M-MLV(RNase H-) | 0.25-1 µL |
| RNase-free water | Make up to 12 µL |

(3) Centrifuging and mixing for a few seconds, and performing PCR. The procedure is: 42° C., 60 min; 70° C., 15 min.

5. Cloning of Intermediate Fragment

Obtain target fragment through high-fidelity enzyme amplification of PrimeSTARHS. The PCR reaction system is as follows.

TABLE 4

PCR reaction system

| Reagent | Volume |
| --- | --- |
| PrimeSTARHS | 5 µL |
| Template | 0.4 µL |
| Upstream primer | 0.4 µL |
| Downstream primer | 0.4 µL |
| ddH$_2$O | 3.8 µL |
| Total | 10 µL |

A three-step method was used for amplification. The PCR reaction procedure is as follows:

| 94° C. | 5 min | |
| --- | --- | --- |
| 98° C. | 15 s | |
| Tm value | 30 s | 35 Cycles |
| 72° C. | 1-3 min | |
| 72° C. | 10 min | |

(2) Gel Detection and Recovery of Target Fragments

1 µL of PCR product was aspirated and detected by using 1% agarose electrophoresis, the target fragments were amplified, and the PCR product was recovered according to the instructions of the PCR product recovery kit (Gene JET Gel Extraction Kit).

(3) Ligation of Target Fragments

The purified PCR product was ligated to the pMD-19T Vector (FIG. 1). The system is as follows.

TABLE 5

System

| Reagent | dose |
| --- | --- |
| Solution I | 5 µL |
| Destination segment | 4.5 µL |
| pMD19-T Vector | 0.5 µL |
| Total | 10 µL |

The ligation procedure: Ligation was carried out at 16° C. for about 16 hours.

(4) Transformation

DH5α competent cells were removed from an ultra-low temperature refrigerator, placed on ice till slight solution, and then the ligation product was added to a vial containing 100 µL DH5α competent cells and gently blown for homogeneity. The vial was placed on ice for 30 min and heat shocked at 42° C. for 60-90 s, then was placed on ice and stood for 2-3 minutes. Then 890 µL of LB liquid medium which was preheated at 37° C. in advance was added and incubated under vibration at 37° C., 200 rpm for 1 h, then 4000 rpm for 2 minutes. The supernatant was discarded, leaving about 100 μL. The suspended cells were gently blown and smeared on the LA (Amp+) solid plate. Finally, the cells was incubated upright for half an hour at 37° C., then incubated inverted overnight.

(5) Colony PCR Detection

A single colony was picked and inoculated in LA (containing Amp+) liquid medium, incubated under vibration at 37° C., 220 rpm for about 6 hours. M13 universal primers were used to identify positive clones, and the positive colonies detected by 1% agarose gel electrophoresis were sent to Guangzhou Shenggong for sequencing. The specific system and procedures are as follows:

TABLE 6

| System | |
|---|---|
| Premix Taq | 5.0 μL |
| Primer M13-F(10 μM) | 0.4 μL |
| Primer M13-R(10 μM) | 0.4 μL |
| Bacteria culture solution DNA | 0.4 μL |
| ddH$_2$O | 3.8 μL |
| Total | 10 μL |

TABLE 7

| Procedure | | |
|---|---|---|
| 94° C. | 5 min | |
| 94° C. | 30 s | |
| 54° C. | 30 s | 30 cycles |
| 72° C. | 2 min | |
| 72° C. | 10 | |

6. 3'- and 5'-Terminal RACE Amplification

The 3'- and 5'-RACE cDNA template was prepared by referring to the instructions for SMART™ RACE cDNA Amptification kit. Nested PCR was performed for amplification by binding 3'- and 5'- specific primers to universal primers (NUP and UPM).

The first round of RACE response

TABLE 8

| System | |
|---|---|
| Reagent | Volume |
| PrimeSTAR HS | 5 μL |
| 3'/5'cDNA template | 0.4 μL |
| UPM primer | 0.4 μL |
| Outer specific primer | 0.4 μL |
| ddH$_2$O | 3.8 μL |
| Total | 10 μL |

PCR reaction procedure:

| 94° C. | 5 min | |
|---|---|---|
| 98° C. | 15 s | |
| Tm | 30 s | 30 Cycles |
| 72° C. | 3 min | |
| 72° C. | 10 min | |

(2) Second Round of RACE Response

TABLE 9

| System | |
|---|---|
| Reagent | volume |
| Premix Taq | 5 μL |
| 3'/5'cDNA template | 0.4 μL |
| NUP primer | 0.4 μL |
| Inner specific primer | 0.4 μL |
| ddH$_2$O | 3.8 μL |
| Total | 10 μL |

PCR reaction procedure:

| 94° C. | 5 min | |
|---|---|---|
| 94° C. | 30 s | |
| Tm | 30 s | 35 Cycles |
| 72° C. | 2 min | |
| 72° C. | 1 min | |

(3) PCR gel cutting recovery/product purification: ligation, transformation and colony PCR detection may be referred to steps (2)-(5) in the above section 5.

7. Bioinformatics Analysis

NCBI blastx was used for sequence homology and similarity analysis, DNAMAN 6.0 software was used sequence search, splicing and alignment, ExPASy was used for online prediction of its theoretical molecular weight (MW) and isoelectric point (pI), SignalP 4.0 Server was used for signal peptide sequence prediction, TMHMM Server v. 2.0 was used to analyze the transmembrane domain of the sequence, MEGA 6 software was used to construct a phylogenetic tree by using a NJ method, SoftBerry Psite was used to predict the functional site of its deduced amino acid sequence, and SOPMA was used to predict the secondary structure of the protein.

8. Tissue Expression and Temporal Expression Analysis after PAMPs Stimulation 8.1 Shellfish Treatment and Sample Collection Tissue quantification: Ten vigorous P.f. martensii with the same size, were selected and the tissues of gonads, gills, mantle membrane, hemolymph, adductor muscle and hepatopancreas were collected.

(2) PAMPs stimulation: 320 healthy P.f. martensii kept for 1 week and randomly divided into 4 groups: LPS stimulation group (experimental group), PGN stimulation group (experimental group), PolyI:C stimulation group (experimental group)), and PBS group (control group), with 80 shells in each group. A method of adductor muscle injection was used, each P.f. martensii in the experimental group was injected with 100 μL of LPS, PGN, PolyI:C (10 μg/mL), and 100 μL of PBS was injected in the control group. At 0, 3, 6, 12, 24, 48, 72, 96 h after injection, 10 shellfishes were randomly selected from each group and whole tissues were taken out for later use. The hemolymph is centrifuged at 4° C., 800× g for 15 minutes, and the supernatant discarded, and 1 mL Trizol was added and gently shaken to mix the suspension uniformly. Total RNA was extracted and reverse transcribed into cDNA for the following quantitative analysis (Note: PBS was sterilized, LPS, PGN, PolyI:C were prepared using sterilized PBS. No bait was fed, and no death occurred during the experiment).

8.2 Primer Design
The primers used in the fluorescence quantitative PCR reaction are shown in Table 1.

8.3 Extraction of Total RNA
The method for extraction of total RNA is the same as that in steps of (1)-(4) in section 3.

8.4 Preparation of Fluorescence Quantitative cDNA Template
Operation was followed according to the instructions of Reverse Transcriptase M-MLV (RNase H).

RNA was bound to the primers: The PCR procedure was 70° C., 10 min, and placement on ice for 2 to 3 min. The sample addition system is as follows:

TABLE 10

| Sampling system | |
|---|---|
| Reagent | volume |
| Total RNA | 1 ng-1 μg |
| Random Primers(25 uM) | 1 μL |
| RNase-free water | Make up to 8 μL |

(3) The following reagents were added to the above RNA system:

TABLE 11

| Reagents | |
|---|---|
| Reagent | dose |
| 5 × M-MLV Buffer | 2.0 μL |
| dNTP Mixture(10 mM) | 0.5 μL |
| RNase Inhibitor | 0.25 μL |
| RTase M-MLV(RNase H-) | 0.25-1 μL |
| RNase-free water | Make up to 12 μL |

(3) Centrifugation and mixing was performed for a few seconds, and PC was performed. The procedure was 42° C., 60 min; 70° C., 15 min, the obtained first strand of cDNA was stored at −20° C.

8.5 Fluorescence Quantitative PCR
The reverse transcription cDNA in section 8.4 was used as the template, and GAPDH was selected as the internal reference gene. Sample wells were set based on 3 experimental replicates. Real-time fluorescence quantitative PCR was performed according to the following reaction system and reaction conditions:

TABLE 12

| Reaction system | |
|---|---|
| Forward Primer | 0.5 μL |
| Reverse Primer | 0.5 μL |
| Template | 0.5 μL |
| SYBR Premix ExTaqTM | 5 μL |
| dd H₂O | 3.5 μL |
| Total | 10 μL |

Reaction procedure:

| | | |
|---|---|---|
| 95° C. | 2 min | |
| 95° C. | 15 s | |
| 60° C. | 60 s | 40 cycles |
| 72° C. | 30 s | |
| 95° C. | 10 s | |
| 65° C. | 60 s | Melt Curve |
| 97° C. | 1 s | |
| 37° C. | Cool 30 s | |

8.6 Statistics and Analysis
The fluorescence quantitation data was analyzed using a $2^{-\Delta\Delta ct}$ method. The test results were all expressed as mean±standard deviation, and SPSS17.0 software was used to perform one-way ANOVA, and Duncan's multiple range test was used to test the significance of differences in the mean values.

9. Preparation of Recombinant Protein
9.1 Gene Synthesis
Gene synthesis was performed according to the existing target gene sequence, which was used as a template for subsequent subcloning, and the introduced restriction sites were NcoI and HindIII.

9.2 Construction of Prokaryotic Expression Vector
Amplification of recombinant PmTLS ORF. The PCR system was: 10 μL of Premix Ex of Taq, 0.5 μL synthesis template, Forward Primer and Reverse Primer 0.4 μL for each, the system was made up to 20 μL by using ddH₂O. The procedure was: denaturation at 94° C. for 5 min; 98° C. for 10 s, 55° C. for 30 s, 72° C. for 60 s, 30 cycles. The reaction products were detected by gel electrophoresis.

See section 5 for cloning and sequencing of PmTLS and PmKuPI.

Extraction of plasmid may be referred to the instructions of the Easy Pure Plasmid Mini Prep Kit (Silica Gel Membrane Spin Column Plasmid DNA Mini Extraction Kit).

Double digestion of the empty plasmid pET-28a(+) and the extracted recombinant plasmid with MluI, XhoI and HindIII endonucleases was performed. The system was: 5.0 μL of 10× FD Buffer, M1uI endonuclease 3.0 μL, 20 μL of plasmid, and ddH₂O to make up the system to 50 pt. Mix lightly and keep at 37° C. for 2 h.

The purification of gel cutting may be refer to step (2) in section 2.2.5.

The recovered product purified by restriction digestion was ligated to the pET-28a(+) vector through the action of T4 ligase to construct the recombinant expression plasmid pET28a-PmTLS. System for ligation was as follows: recovered digested and purified product: 6 μL, pET-28a (+): 2 μL, 10× Buffer T4: 1 μL, T4 ligase: 1 μL, total volume of the system: 10 μL. The reaction mixture was mixed gently and allowed to react overnight at 16° C.

Transformation of the ligation product, screening of positive clones, and the sequencing may be referred to the steps (4) to (5) in Section 5.

Plasmid extraction may be referred to step (3) in Section 9.2 to obtain the pET28a-PmTLS recombinant plasmid, which was stored at −20° C. for later use.

9.3 Induced Expression of Recombinant Fusion Protein
Transform and Screening of Positive Clones Competent cell BL21 (DE3) was taken out of the ultra-low temperature refrigerator and thawed in ice firstly. 100 ng of plasmid DNA was added to the BL21 (DE3) strain and mixed gently. The test tube was placed on ice and incubated for 30 minutes, and the tube heated at 42° C. for 90 seconds without shaking. The test tube was placed on ice for 3 minutes, and 100 μL of room-temperature LB medium was added. The tube was shaken and incubated at 200 rpm at 37° C. for 60 minutes, the resulting mixture was spread on an LB agar plate containing 50 μg/mL of kanamycin, and the plate was inverted and incubated at 37° C. overnight. Positive clones were screened and sequenced.

Best Induction Conditions Selected the for Small-Scale Culture

Three well-separated single colonies were picked and each inoculate into 4 mL LB medium containing 50 µg/mL kanamycin, and the cells was incubated on a shaker at 37° C. with 200 rpm shaking. When the OD600 value reached 0.6-0.8, IPTG was added to two of the three tubes till a final concentration of 0.5 mM of IPTG. Then the IPTG was induced at 15° C. for 16 h and at 37° C. for 4 h, and third test tube was used as a negative control.

Preparation and Detection of Recombinant Protein and
- a). The cell pellets were harvested from 450 µL of culture and lysed for 1 minute with a sonicator.
- b). Whole cell lysate: 50 µL of 5× loading buffer was mixed with 100 µL of cell lysate and used as a sample of whole cell lysate, and the sample was heated at 100° C. for 10 min, and then centrifuged at 15,000 rpm for 5 min.
- c) Supernatant and debris of cell lysate: the remaining 200 µL of cell lysate was centrifuged at 15,000 rpm for 10 minutes, the supernatant and cell debris of the cell lysate were collected and 90 µL of 5× loading buffers were mixed with 180 µL of supernatant respectively, and used as a sample. The Supernatant of cell lysate. All pellets were re-suspended in 150 µL of 5× loading buffer and used as the sample of cell lysate debris. The samples were heated at 100° C. for 10 minutes and centrifuged at 15,000 rpm for 5 minutes before sample loading.
- d) The expression and solubility of the protein were measured through SDS-PAGE and Western blot, and fusion protein was finally expressed through induction in a large amount.

9.4 Separation and Purification of Fusion Protein

Ultrasonic Disruption of Bacteria

The collected bacteria cells were dissolved in Buffer (50 mM Tris, 150 mM NaCl, 5% glycerol, pH 8.0) and ultrasonically disrupted in an ice bath for 30 minutes at power 350 W (with ultrasound for 4 and pause for 6 s as one cycle).

After sonication, centrifugation was performed for 20 min at 12,000 rpm, 4° C., the supernatant was discarded. The precipitates were disrupted and dissolved in Buffer, ultrasonically disrupted in an ice bath for 30 min at a power 350 W (with ultrasound for 4 s and pause for 6 s as one cycle).

After sonication, centrifugation was performed for 20 min at 12,000 rpm, 4° C., and the supernatant was collected for the next step of purification.

Nickel Agarose Affinity Chromatography 5 mL of Ni-NTA was taken and the column was washed and equilibrated with Binding buffer of 5 volumes of the column bed at a flow rate of 5 mL/min.

The filler and the sample were loaded on the column after being incubated for 1 hour and the eluate was collected.

The column was washed with Binding buffer 5 volumes of the column bed at a flow rate 5 m L/min.

The impurities were washed off with Washing buffer at a flow rate of 5 mL/min, and the eluate was collected.

Elution was carried out with Elution buffer at a flow rate 2 mL/min, and the eluate was collected.

Samples were collected for SDS-PAGE detection.

SDS-PAGE Detection of Purified Protein

Preparation of 12% SDS-PAGE: Tris-Gly electrophoresis buffer was used and electrophoresis was conducted for 20 min in stacking gel at 80 V and for 60 min in separating gel at 120 V. After the completion of the gel electrophoresis, the gel was stained with Coomassie blue for 20 min and then decolorized overnight.

Western Blot Detection

Gel preparation: preparation of polyacrylamide gel: 5% for stacking gel and 12% for separating gel.

Sample preparation: sample loading.

Electrophoresis: stacking gel, 80 V, 30 min; separating gel 120 V, 60 min.

Membrane transfer: wet transfer, 250 mA, 90 min.

Blocking: 5% skimmed milk powder was used and conducted at 37° C. for 2 hours on slow shaking.

Incubation of the primary antibody: the primary antibody was rabbit anti-his-tag available from the antibody company of Sangon Biotech, NO.: D110002, 1:500 dilution, 37° C.; the primary antibody was slowly shaken for 60 min.

Incubation of secondary antibody: goat anti-rabbit secondary antibody, available from the antibody company of Sangon Biotech, NO.: D110058, 1: 8000 dilution, 37° C.; the secondary antibody was slowly shaken 60 min.

Color development: developed with TMB.

Renaturing of Inclusion Body Protein

The purified target protein was renatured by dialysis, and finally replaced with a soluble buffer (PBS, 10% glycerol, 1 ML-arginine, pH 7.4), and the purity of the purified protein before renaturation (precipitation) and after renaturation (dissolution) was detected and compared by SDS-PAGE and Western blot.

Testing of Antibacterial Activity of the Purified Protein

The antibacterial activity of the purified protein against *Escherichia coli, Micrococcus luteus, A. hydrophila, P. aeruginosa, V. parahaemolyticus, V. harveyi, Bacillus subtilis* and *Staphylococcus aureus* was tested. First, each species of bacteria was cultured in 2216E liquid medium to a logarithmic growth phase. Then the bacteria were centrifuged (3,000× g, 10min), washed 3 times with phosphate buffered saline (1× PBS), and then resuspended in PBS. Second, a 96- well microtiter plate was used to mix 50 µL of purified protein (200 µg/mL) with 10 µL of each bacterial suspension, and the mixture was incubated at room temperature for 2 hours. PBS was used as a negative control. Then 140 µL of medium was added to each mixed well, incubated in a constant temperature incubator at 37° C., and a microplate reader (EnSpire, PerkinElmer) was used to measure the OD600 value at hour 0, 1, 2, 3, 4, 5, 6, 7, 8, 9, 10, 11 and 12 after adding purified protein and PBS. Three experiments were performed in parallel for each sample.

j) Observation of Morphological Changes of the Bacteria after Being Effected by the Purified Protein with Transmission Electron Microscope 200 µL of bacteria in the exponential growth phase was treated with 200 µL of purified protein at 37° C. for 2 hours. PBS was used instead as a control. Then mixture of the purified protein and the bacterial was precipitated through centrifugation for 10 min at room temperature at 3000 rpm and washed with PBS washed 3 times to remove impurities. Then the bacterial precipitates were immobilized overnight with 200 µL of 3% glutaraldehyde. After this treatment, 200 µL of 2% sodium phosphotungstate aqueous solution was added to the bacterial suspension, and the resulting suspension was dripped on the copper mesh. Residual water was removed with filter paper. After 5 minutes, the sample was air-dried and observed with JEM-1400 (Japan Electronics Corporation) microscope under standard operating conditions.

12. Results
12.1 Gene Cloning of PmTLS

A PmTLS gene (SEQ ID No. 1) with a full length of 778 bp was obtained by a RACE cloning technique, which contains 420 bp of the 5'UTR, 97 bp of 3'UTR, 261 bp of ORF frame and encodes 86 amino acids (of SEQ ID No. 2).

12.2 Analysis of Physical and Chemical Properties of PmTLS

Figure 2:
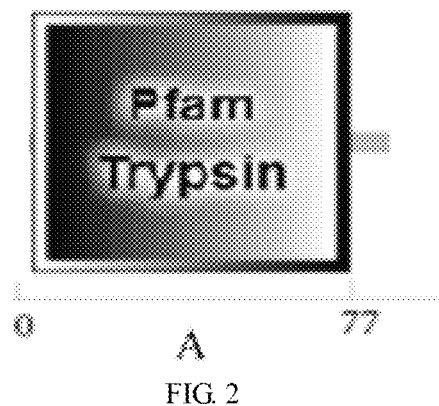
FIG. 2 shows the prediction of the PmTLS domain.
Figure 3A:
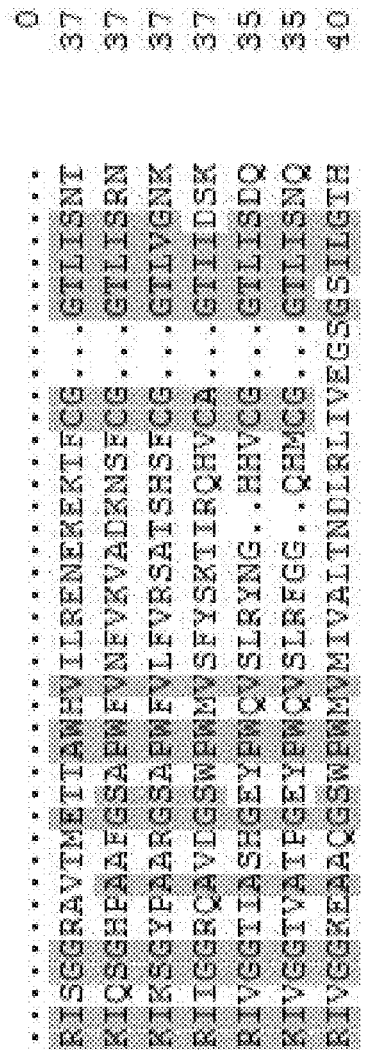
FIG. 3 shows the homology alignment for PmTLS.
Figure 3B:
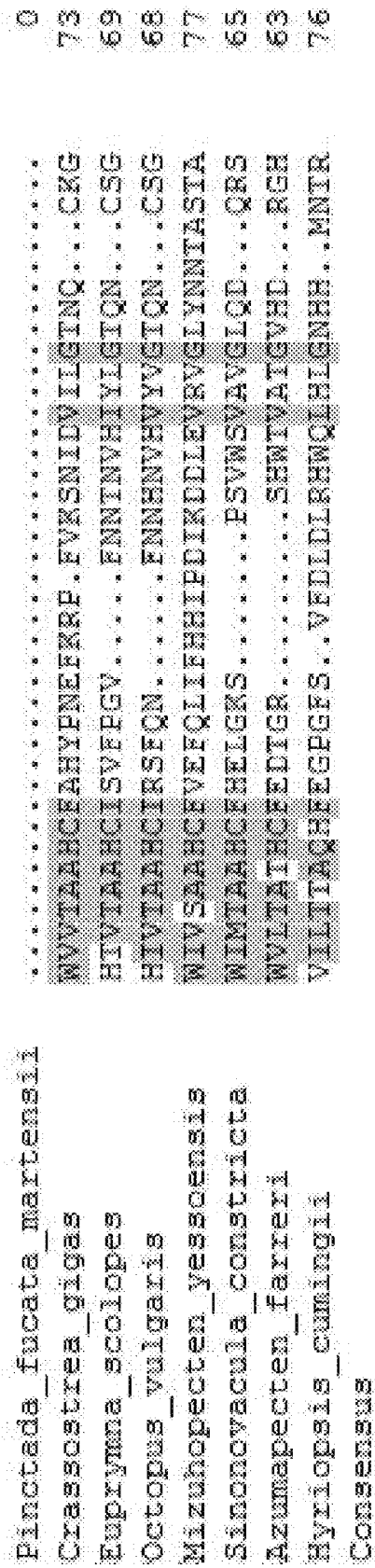
Figure 3F:
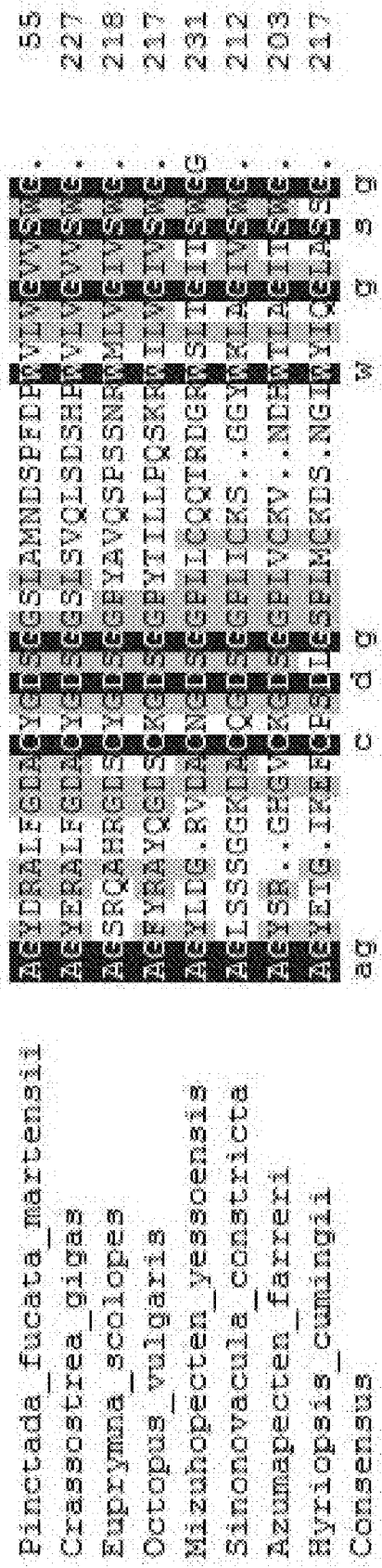
Figure 3G:
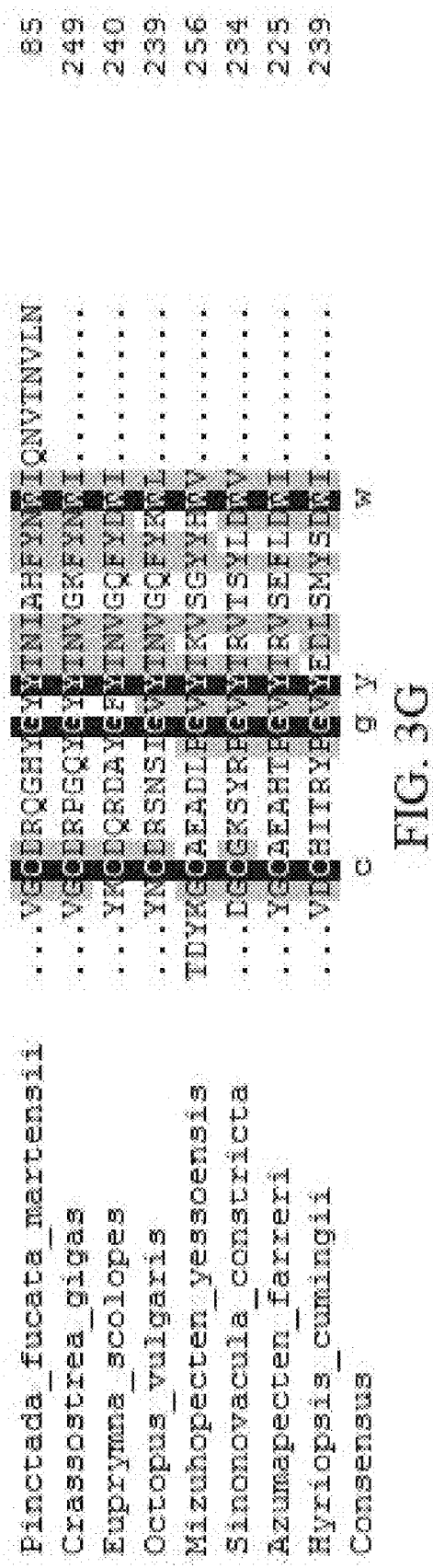

The molecular weight of PmTLS protease is 9.5 KDa and the theoretical isoelectric point is 4.22. It is predicted that its hydrophilic. It is found that the highest continuous hydrophobicity occurs at positions 51 and 52, with an index of 2.011 and the highest hydrophilicity at position 63, with an index of −2.156, and the total average hydrophilicity coefficient is −0.172, which indicating it is a hydrophilic protein. The total number of negatively charged residues (Asp+Glu) is 9 and the total number of positively charged residues (Arg+Lys) is 3. Therefore, the overall PmTLS protease is negatively charged. The prediction of transmembrane structure reveals that it has no transmembrane domain. The secondary structure predicted by SOPMA software shows that random coils account for 39.53% of the whole, a-helical structure for 29.07%, extended chain for 22.09%, and β-turn angle for 9.30%. SMART analysis results show that PmTLSThe amino acid sequence forms a Trypsin domain at positions 1-77 (FIG. 2).

12.3 Homology Analysis of PmTLS

Through DNAMAN, the amino acid sequence of PmTLS was compared with the corresponding amino acids of other invertebrates. It was found that there was highest similarity between PmTLS and Pacific oyster (*Crassostrea gigas*), reaching 69.77%, and the similarity between species reached 41.42% (FIG. 3). The similarity reveals the degree of sequence conservation in the progress of evolution for respective species, and the amino acid sequences of *Pinctada fucata martensii, Crassostrea gigas, Euprymna scolopes, Octopus vulgaris, Mus musculus, Homo sapiens, Geospiza fortis, Zonotrichia albicollis, Oryzias latipes,* and *Fundulus heteroclitus* are shown in SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, and SEQ ID NO. 22.

Figure 4:
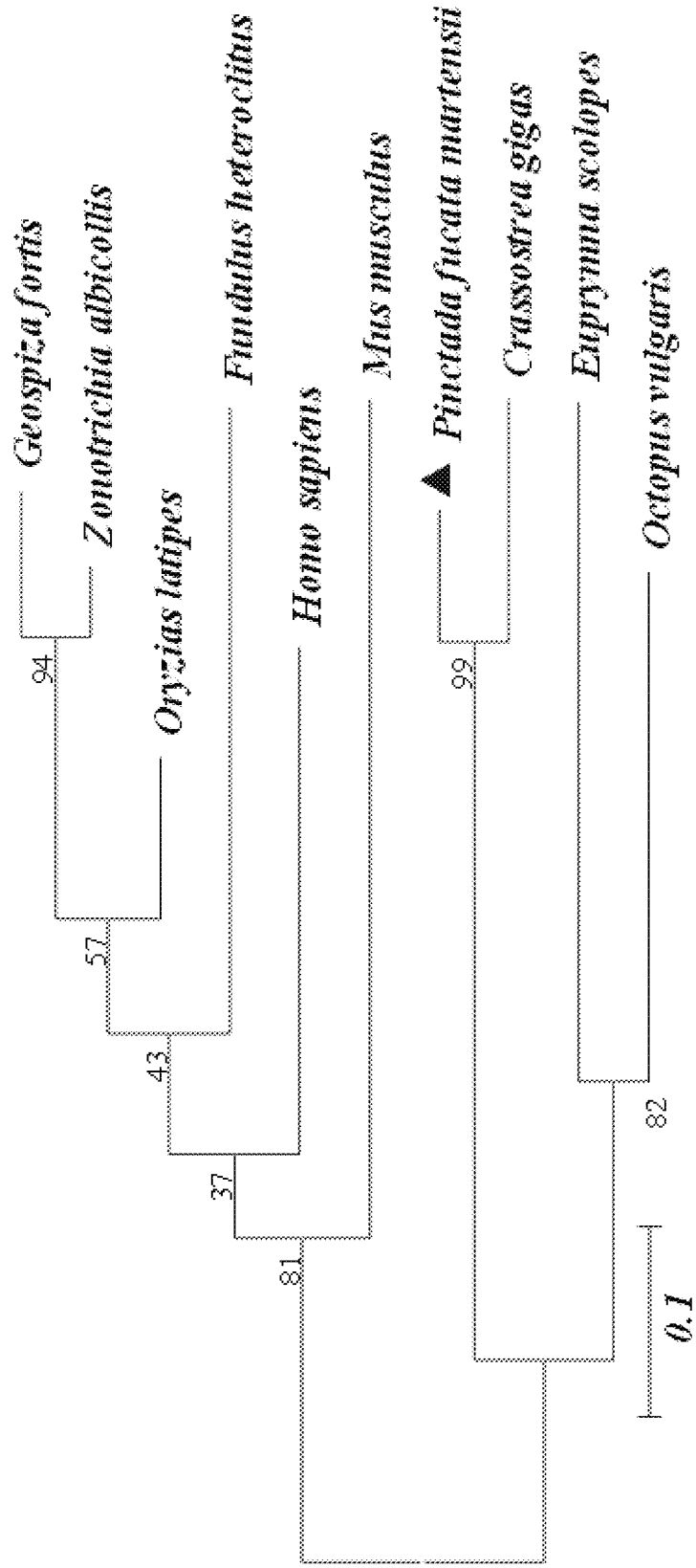
FIG. 4 shows the construction of PmTLS phylogenetic tree.

MEGA 6 was used to construct a phylogenetic tree. In the phylogenetic tree classification of PmTLS, it was found that invertebrates clustered into a large branch, and vertebrates clustered into a large branch, and the *P.f. martensii* had the closest relationship with the Pacific oyster (FIG. 4).

12.4 Tissue Quantitative Analysis of PmTLS Gene mRNA

Figure 5:
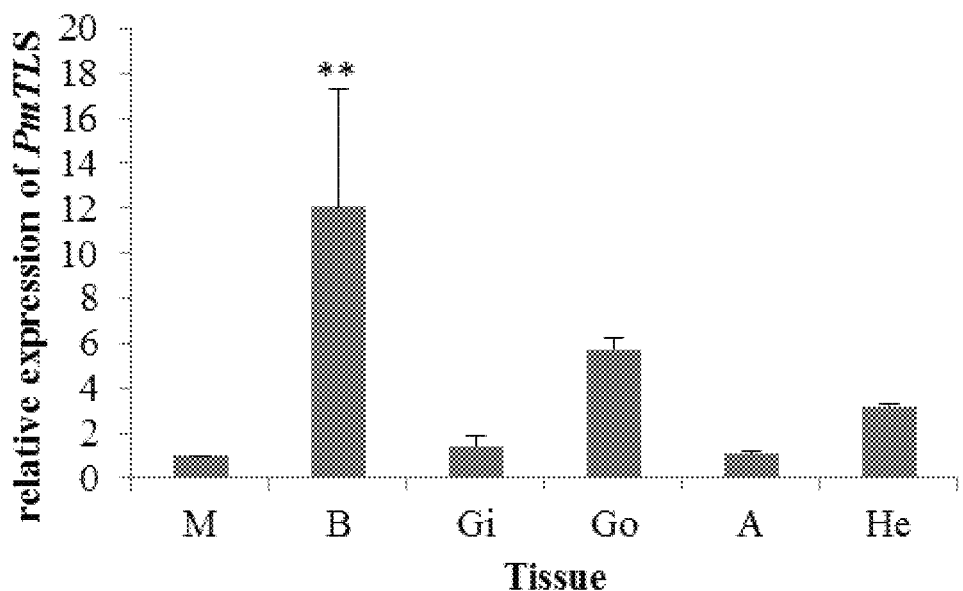
FIG. 5 shows the expression profile of PmTLS gene in respective tissue of *Pinctada facata martensii,* M: mantle, B: hemocytes, Gi: gills, Go: gonads, A: adductor muscle, He: hepatopancreas.

Real-time PCR was use to detected the expression mode of gene mRNA of PmTLS protease in 6 tissues such as hemocytes of the Pinctada martensi. The results showed that PmTLS protease gene had the highest expression level (p<0.01) in hemocytes, followed by the gonads; the expression level in the mantle and adductor muscle was the lowest, with almost no expression (FIG. 5).

Figure 6:
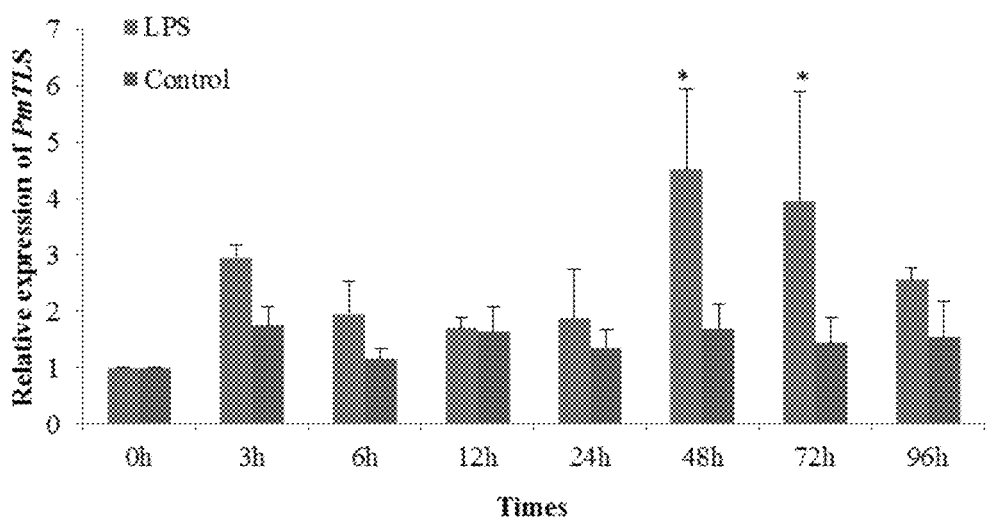
FIG. 6 shows the temporal expression of PmTLS in hemocytes after PAMPs is stimulated.
Figure 7:
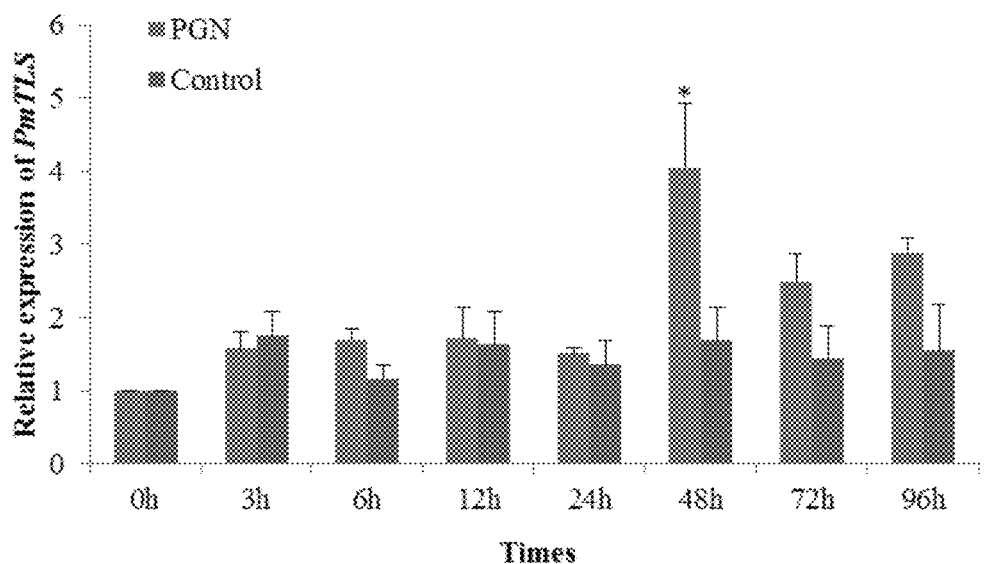
FIG. 7 shows the temporal expression of PmTLS in hemocytes after PAMPs is stimulated.
Figure 8:
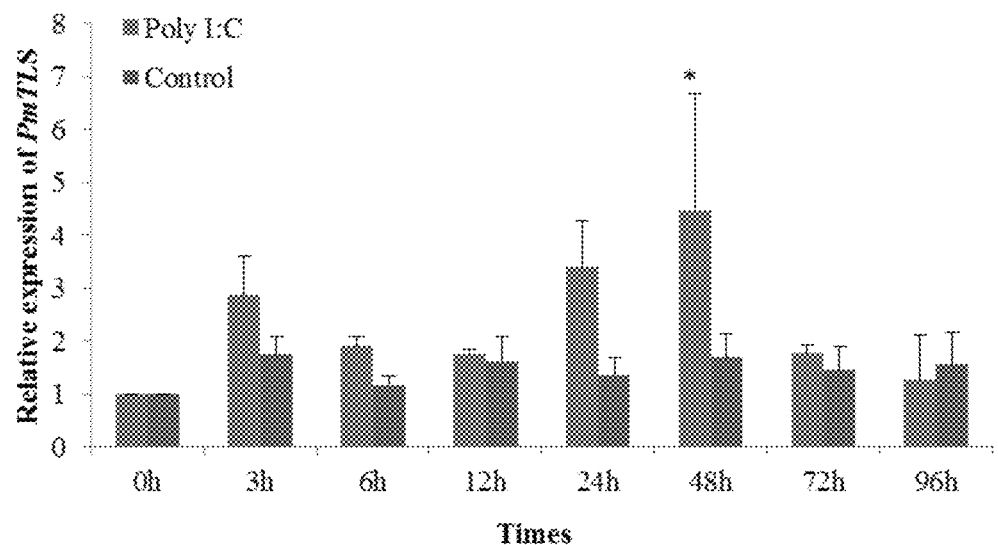
FIG. 8 shows the temporal expression of PmTLS in hemocytes after PAMPs is stimulated.

12.5 Analysis of Temporal Expression of mRNA for PmTLS Gene in Hemocytes after PAMPs Stimulation LPS (lipopolysaccharide), PGN (peptidoglycan) and PolyI:C (polyinosinic acid) and other pathogen-related molecular patterns (PAMPs) was selected to activate the innate immune response of *P.f. martensii*. Real-time PCR detected the temporal changes of mRNA for PmTLS in the hemolymph of *P.f. martensii* at different times. The results showed that, when compared with the control group, after LPS stimulation, PmTLS gene expression increased at 3 h, then remained normal at 24 h, suddenly increased to the maximum at 48 h (P<0.05), and decreased slightly at 72 h and was close to the normal level at 96 h (FIG. 6). PmTLS gene expression remained unchanged within 24 h after PGN stimulation, and reached the maximum expression level directly at 48 h (P<0.05), and began to decrease at 48 h, while there was an upward trend again at 96 h (FIG. 7). After PolyI:C stimulation, the gene expression level of PmTLS began to rise at 24 h, and reached the highest expression level at 48 h (P<0.05), and returned to normal level at 72 h (FIG. 8).

12.6 Expression of PmTLS Recombinant Protein

Construction of PmTLS Prokaryotic Expression Vector

Figure 9:
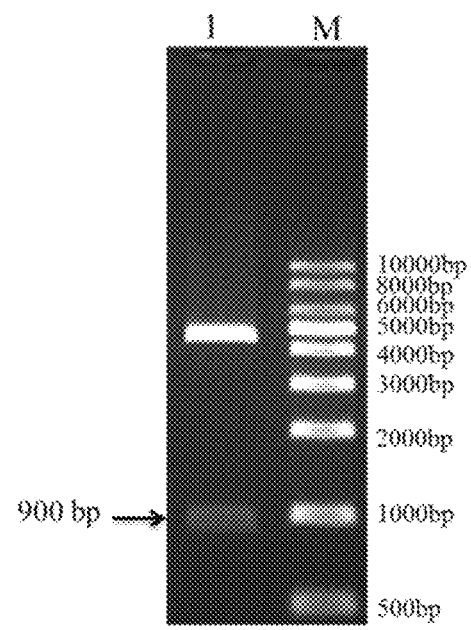
FIG. 9 shows the identification of recombinant plasmid for PmTLS prokaryotic expression.

According to the existing full-length cDNA sequence of the PmTLS gene, the open reading frame ORF was predicted and analyzed to obtain the ORF sequence that needed to be recombined. Histidine gene sequence was designed and added to the recombination ORF sequence, and gene synthesis was followed, and then prokaryotic expression primers were designed. After PCR amplification, the PmTLS gene fragment had a length of about 290 bp, then the PmTLS gene was ligated to the MD19-T vector, transformed, and a single colony was selected. The colonies of positive clones were identified by colony PCR, and the biogenic plasmid extraction kit was used to extract the plasmid and digested with MluI endonuclease. And PmTLS was ligated to the pET-28a(+) vector, transformed, and positive clones were identified by colony PCR. The gene fragments of PmTLS after M1uI digestion had a length of about 900 bp. Subsequently, the plasmids with positive clone results were extracted, and the plasmids obtained by extraction were the recombinant plasmids of pET28-PmTLS. The estimated molecular weights of the recombinant proteins were 10.32 KDa. The results for colony PCR identification, MluI digestion identification (FIG. 9) and sequencing confirmed that the pET28-PmTLS vector was successfully constructed.

Induced Expression of PmTLS Recombinant Protein (rPmTLS)

Figure 10:
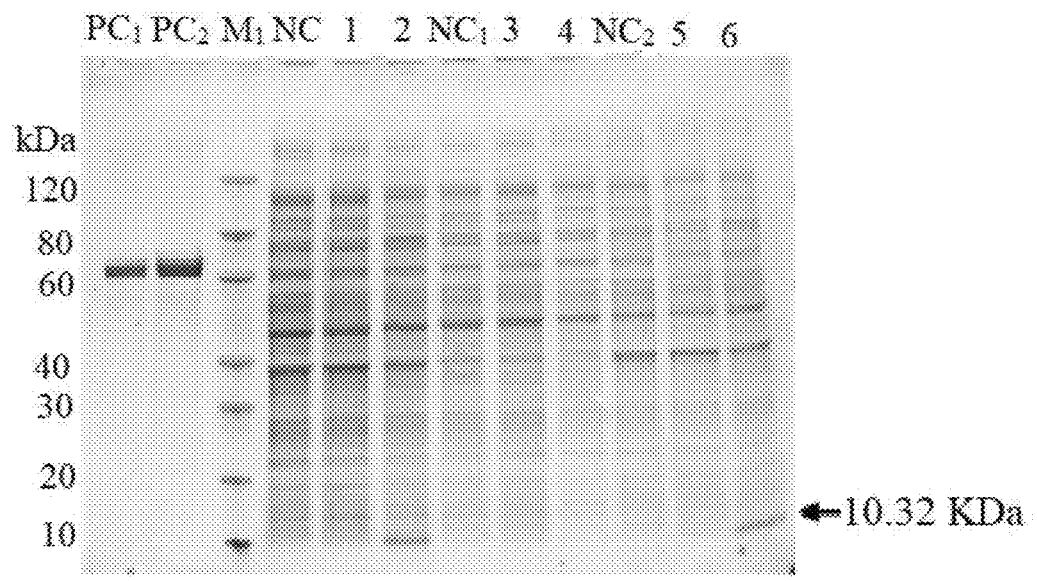
FIG. 10 shows the induced expression of rPmTLS (SDS-PAGE), PC1: BSA (1 μg); PC2: BSA (2 μg); M1: Marker; NC: non-induced whole bacteria; 1: 15° C. induced whole bacteria; 2: whole bacteria induce at 37° C.; NC1: non-induced supernatant; 3: supernatant induced at 15° C.; 4: supernatant induced at 37° C.; NC2: non-induced precipitation; 5: precipitation induced at 15° C.; 6: precipitation induced at 37° C.
Figure 11:
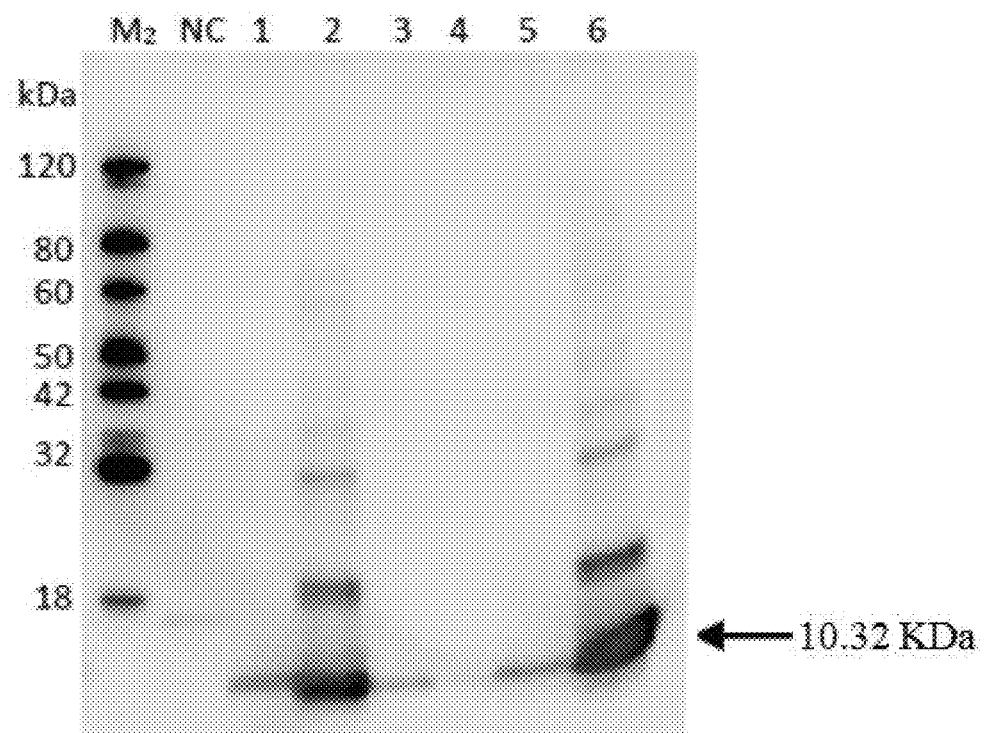
FIG. 11 shows the induced expression of rPmTLS (Western Blot), M2: Marker; NC: non-induced whole bacteria; 1: whole bacteria induced at 15° C.; 2: whole bacteria induced at 37° C.; NC1: non-induced supernatant; 3: induced supernatant induced at 15° C.; 4: supernatant induced at 37° C.; 5: precipitation induced at 15° C.; 6: precipitation induced 37° C.

The recombinant expression vector pET28-PmTLS was transformed into *E. coli*, with 0.5 mM of IPTG, induced at 15° C. for 16 h and 37° C. for 4 h, respectively, wherein a negative control without IPTG induction was used. It can be seen from FIG. 9 that the no target bands appear in lanes NC (whole bacteria), NC1 (supernatant) and NC2 (precipitates) in the negative control group. At the same time, no target bands were seen in the supernatant lanes 3 and 4 for 15° C. and 37° C. No target bands were seen in lanes 1 (whole bacteria) and 5 (precipitates) for 15° C., distinct target bands appeared in lanes 2 (whole bacteria) and 6 (precipitates) for 37° C. (FIG. 10). Western blot was used to further verified the results and the results showed that a clear single staining band appeared at about 10 KDa in lanes 2 (whole bacteria) and 6 (precipitation) induced at 37° C., which was consistent with the theoretical value of 10.32 KDa, indicating that a higher purity recombinant protein was successfully obtained (FIG. 11). The results show that rPmTLS has an optimal induction temperature of 37° C., and it is mainly expressed as inclusion bodies.

Figure 12:
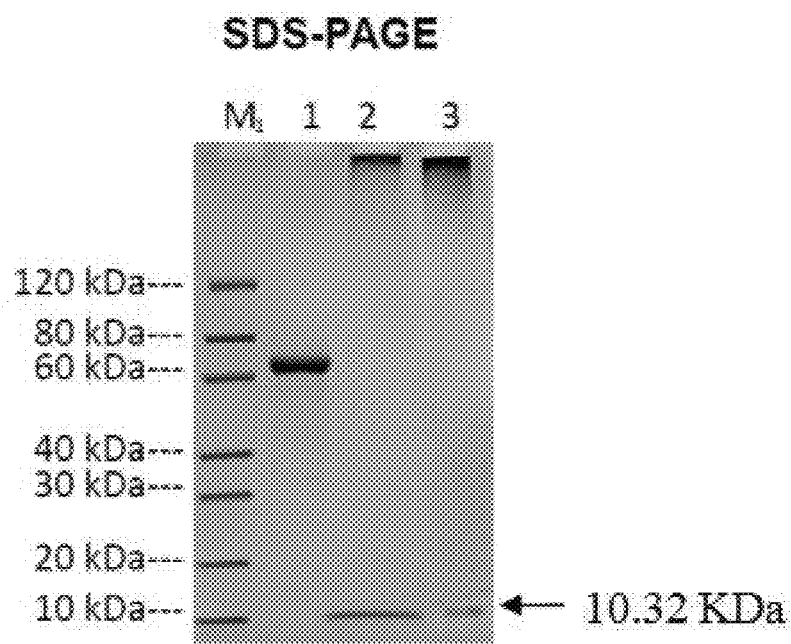
FIG. 12 shows the purification analysis (SDS-PAGE) of rPmTLS; M1: Marker; 1: BSA (2 μg); 2: target protein after renaturation (2 μg); 3: target protein before renaturation (2 μg)
Figure 13:
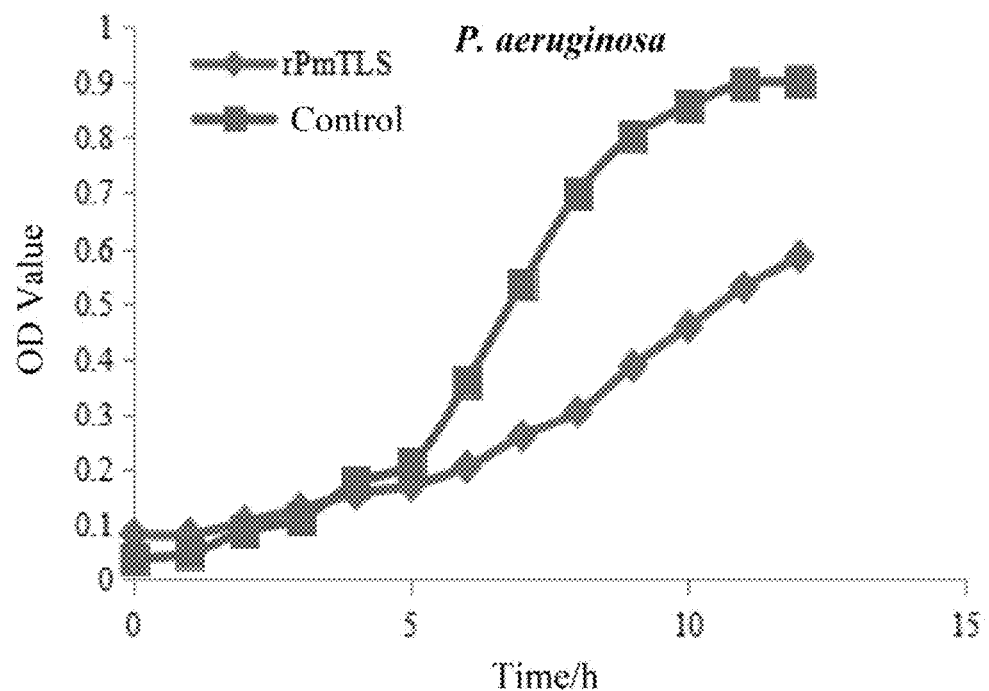
FIG. 13 shows the determination of the antibacterial activity of rPmTLS (*P. aeruginosa*)
Figure 14:
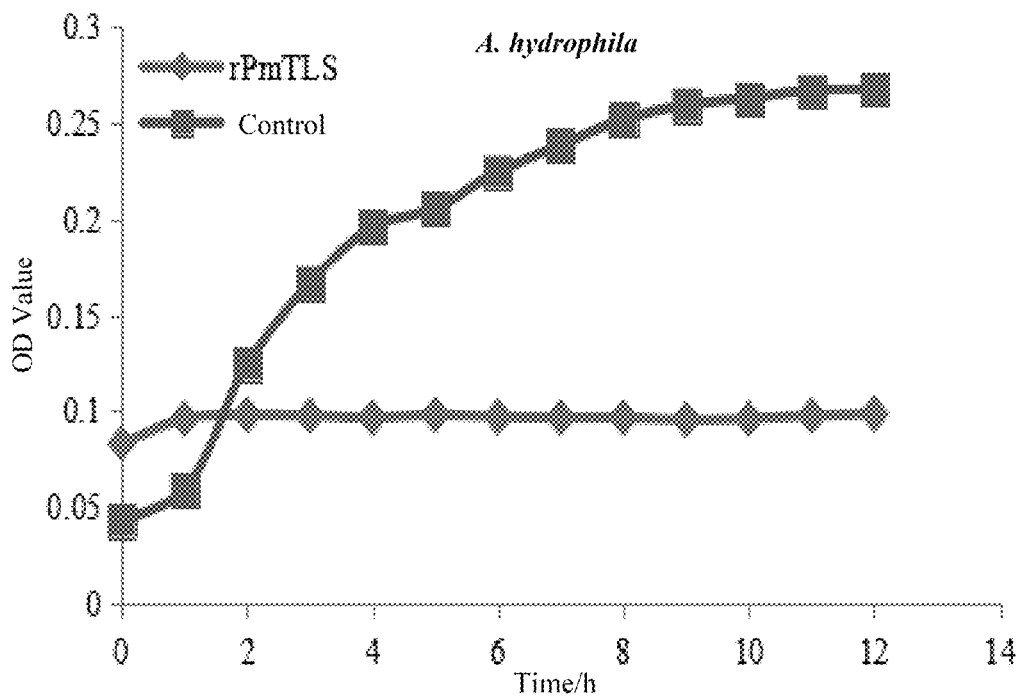
FIG. 14 shows the determination of the antibacterial activity of rPmTLS (*A. hydrophila*)
Figure 15:
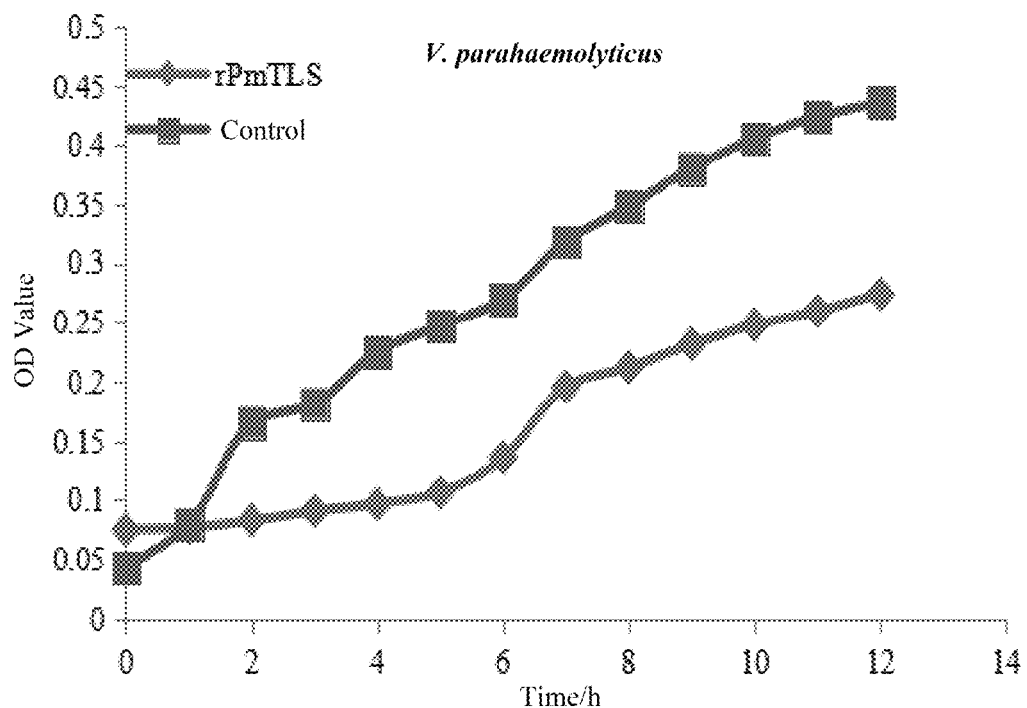
FIG. 15 shows the determination of antibacterial activity of rPmTLS (*V. parahaemolyticus*)
Figure 16:
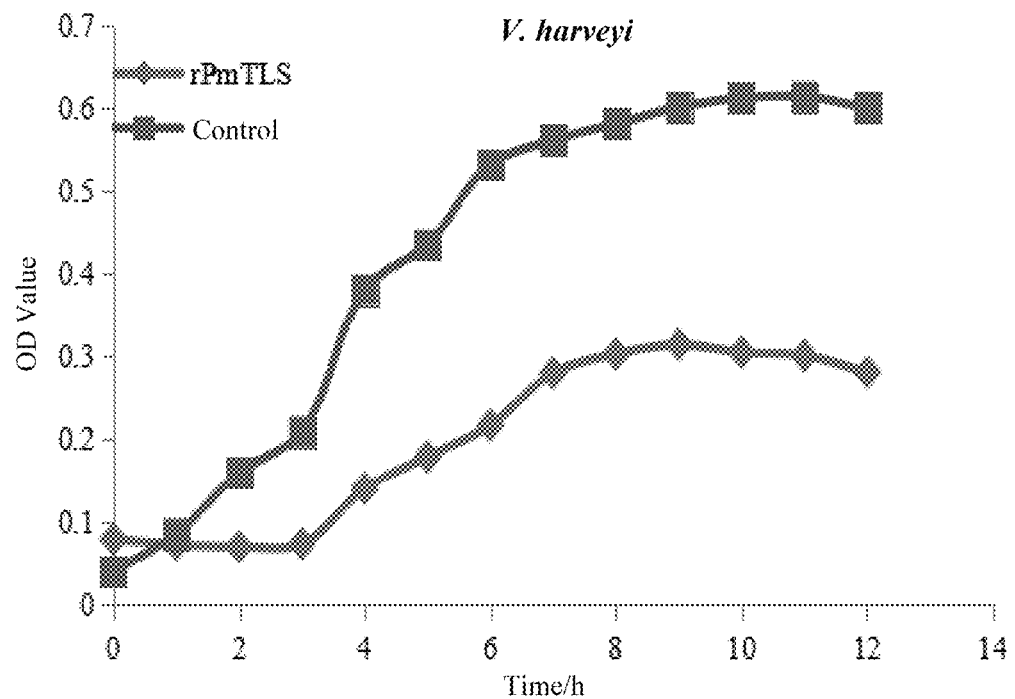
FIG. 16 shows the determination of antibacterial activity of rPmTLS (*V. harveyi*)

In order to obtain a large amount of fusion protein, expression strain of pET28-PmTLS was cultured at an expression level of 1 L, and induced at 0.5 mM IPTG at 37° C. for 4 h. The results showed that a clear and single band appeared at about 10 KDa, indicating that rPmTLS with higher purity was successfully obtained, and there was no change in the molecular weight of the recombinant protein before and after renaturation, indicating that higher purity was obtained after renaturation (FIG. 12). The concentration of rPmTLS was determined by Bradford protein assay, and the concentration was 1.07 mg/mL. A total of 8.02 mg protein of rPmTLS was obtained.

12.7 Determination of Antibacterial Activity of rPmTLS

In the inhibition experiment of bacterial liquid growth curve, a total of 8 types of bacteria were determined. Among them, 3 were Gram-positive bacteria, 5 were Gram-negative bacteria, and rPmTLS protein significantly inhibited the growth of 4 Gram-negative bacteria (P<0.05), which are *P. aeruginosa, A. hydrophila, V. parahaemolyticus,* and *V. harveyi* (FIG. 13-16), but they have little effect on the growth of Gram-positive bacteria.

12.8 Antibacterial Mechanism of rPmTLS

In order to understand the antibacterial mechanism of the TLS of *P.f. martensii,* a rPmTLS solution was reacted with *P. aeruginosa, A. hydrophila* and *V. parahaemolyticus* for 2 h, and the mesh was dripped and microscope was performed under a transmission electron microscope. The results are shown in FIG. 17, and it can be seen from the figure that clear and complete edge is seen in the *P. aeruginosa* control group (FIG. 17A), contents are dense and in a uniform shape. It can be observed in the experimental group (FIG. 17B) that the bacteria of *P. aeruginosa* swells, the content of the substance shrinks, and the internal structure is also significantly changed compared with that in the control group. At the same time, it appears that the cell wall begins to dissolve, cytoplasm and cell walls separated from each other, and a plasmolysis phenomenon (shown as FIG. 17C-FIG. 17D in the FIG. 17) occurs, indicating that the cell-wall disintegration leads to the release of local contents in the cell. In FIG. 17 E represents *A. hydrophila* control group, the bacteria have an elongated shape and sharp edges, and uniform content, while in experimental group (FIG. 17F), substance-containing partial loss of content in *A. hydrophila,* and changes in internal structure are observed. In the amplified view of its both ends, the edge is found rather irregularity on the edge of the bacteria and lysis of the cell wall are observed (FIG. 17G, FIG. 17H). In FIG. 17I represents the *V. parahaemolyticus* control group, the bacteria have a short rod shape, and is full and uniform. While in the experimental group (FIG. 17J) the content absence, expansion in middle of the bacteria are observed. When viewing the amplified view of the bacteria, it is further observed that that the cytoplasm separates from the cell wall, and a plasmolysis phenomenon (FIG. 17K) is observed.

Described above are merely the preferred embodiments of the present disclosure. It should be pointed out that for those of ordinary skill in the art, several improvements and modifications can be made without departing from the principle of the present disclosure, and these improvements and modifications should also be regarded as the protection scope of the present disclosure.

What is claimed is:

1. A method for inhibiting a microorganism, the method comprising contacting a protein having the amino acid sequence of SEQ ID No.2 with said microorganism, wherein said microorganism is selected from the group consisting of *Pseudomonas aeruginosa, Aeromonas hydrophila, Vibrio Parahaemolyticus*, and *Vibrio harveyi*.

2. The method according to claim 1, wherein the protein is encoded by a gene for a trypsin-like serine protease, wherein said gene for said trypsin-like serine protease has the nucleotide sequence of SEQ ID No.1.

* * * * *